(12) United States Patent
Spotnitz et al.

(10) Patent No.: US 8,744,601 B2
(45) Date of Patent: Jun. 3, 2014

(54) METHODS FOR OPTIMIZATION OF BIVENTRICULAR PACING DEVICES AND SYSTEMS USEFUL THEREFOR

(75) Inventors: Henry M Spotnitz, New York, NY (US); Thomas A Quinn, Broomfield, CO (US); George Berberian, Merrillville, IN (US)

(73) Assignee: Medtronic, Inc., Minneapolis, MN (US)

( * ) Notice: Subject to any disclaimer, the term of this patent is extended or adjusted under 35 U.S.C. 154(b) by 1980 days.

(21) Appl. No.: 11/910,532

(22) PCT Filed: Apr. 4, 2006

(86) PCT No.: PCT/US2006/012430
§ 371 (c)(1),
(2), (4) Date: Jul. 14, 2011

(87) PCT Pub. No.: WO2006/107922
PCT Pub. Date: Oct. 6, 2012

(65) Prior Publication Data
US 2011/0264159 A1  Oct. 27, 2011

Related U.S. Application Data

(60) Provisional application No. 60/668,015, filed on Apr. 4, 2005, provisional application No. 60/669,680, filed on Apr. 8, 2005, provisional application No. 60/713,237, filed on Aug. 31, 2005.

(51) Int. Cl.
*A61N 1/368* (2006.01)

(52) U.S. Cl.
USPC .......................................................... 607/129

(58) Field of Classification Search
USPC .................................................. 607/129–131
See application file for complete search history.

(56) References Cited

U.S. PATENT DOCUMENTS

| | | | |
|---|---|---|---|
| 5,476,503 A * | 12/1995 | Yang | 607/129 |
| 6,708,061 B2 * | 3/2004 | Salo et al. | 607/9 |
| 6,978,184 B1 | 12/2005 | Marcus et al. | |
| 2001/0031993 A1 | 10/2001 | Salo et al. | |
| 2004/0220637 A1 | 11/2004 | Zdeblick et al. | |

* cited by examiner

*Primary Examiner* — Amanda Patton
(74) *Attorney, Agent, or Firm* — Reed A. Duthler

(57) ABSTRACT

The invention is directed to methods and devices for optimization of biventricular pacing in subjects suffering from heart failure. The invention provides for a method for selection of optimal parameters for permanent pacing, the method comprising: positioning one or more arrays of lead wires in the posterior pericardium of a subject, wherein the arrays are connected to a multiplexing switch, wherein the switch is connected to a computer processor and a biventricular pacemaker; from the computer processor, generating a randomized sequence of: (i) pacing sites (VPS), (ii) right ventricular-left ventricular delays (RLDs), (iii) heart rates (HR); (iv) atrioventricular delays (AVDs), (v) or any combination or permutation thereof; and determining cardiac output in real time, using aortic flow velocity, thereby allowing selection of optimal parameters for permanent pacing.

7 Claims, 22 Drawing Sheets

METHODS FOR OPTIMIZATION OF BIVENTRICULAR PACING DEVICES AND SYSTEMS USEFUL THEREFOR

The invention disclosed herein was made with U.S. Government support under NIH Grant No. HL-4109 from the National Bean, Lung and Blood Institute of the National Institute of Health. Accordingly, the U.S. Government may have certain rights in this invention.

CROSS REFERENCE TO PRIORITY APPLICATION

This application claims priority to PCT application no. PCT/US2006/012430, filed Apr. 4, 2006, which claims priority to U.S. provisional application No. 60/668,015, filed Apr. 4, 2005; U.S. provisional application No. 60/669,680, filed Apr. 8, 2005; and U.S. provisional application No. 60/713,237, filed Aug. 31, 2005; all of which are incorporated by reference herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described herein.

The following abbreviations are used: AV—atrioventricular; AVB—Atrioventricular Block; AVD—Atrioventricular Delay; AF—atrial fibrillation; BiVP—Biventricular Pacing; BL—Baseline Ventricular Pacing Site; CI—Cardiac Index; CO—Cardiac Output; CPB—Cardiopulmonary Bypass; CRT—cardiac resynchronization therapy; DOE—Design of Experiments theory; DDD—dual chamber demand; HR—Heart Rate; HB—heart block; LBBB—Left Bundle Branch Block; LV—Left Ventricle; LVEF—Left Ventricular Ejection Fraction; MAP—Mean Arterial Pressure; OPT—Optimum Ventricular Pacing Site; POPT—optimum protocol; PS—pulmonary stenosis; PV—pressure-volume; RLD—right left delay; RV—Right Ventricle; UFP—ultrasound transit time flow probes; VPS—Ventricular Pacing Site.

BACKGROUND

In biventricular pacing (BiVP), one wire or catheter is implanted in the right ventricle (RV) and another is threaded into a vein, the coronary sinus, which drains into the right atrium (RA) to pace the left ventricle (LV). The coronary sinus catheter is then guided to the lateral or posterior part of the left ventricle. Alternatively, a left ventricular lead can be implanted by thoracotomy (i.e., through a small incision between the ribs, the lead is implanted on the surface of the left ventricle) or even by crossing the atrial septum and inserting the lead inside the left ventricle. Yet, the exact and best position for each catheter position is difficult to determine at the time of insertion. In fact, there are no physiological means to determine the best site at the time of lead placement except possibly the use of echocardiography, which is time consuming and poses a problem in keeping the operative field sterile. Biventricular pacing (BiVP) reverses intraventricular conduction delay (IVCD) and left ventricular (LV) dysfunction (LVD) in CHF from dilated cardiomyopathy (DCM). BiVP is appealing because intraventricular conduction delay (IVCD) and left bundle branch block (LBBB) are intrinsic to advancing dilated cardiomyopathy (DCM) with LV dysfunction (LVD). 2-DE of the RV and LV free walls and interventricular septum (IVS) in DCM suggests that LBBB adversely affects the coordination of LV contraction (LV SYNC) and that BiVP, or "cardiac resynchronization therapy" (CRT), can improve LV SYNC. Many, but not all, patients derive clinical benefit from BiVP, and selection criteria are not fully developed. Insertion of permanent endocardial LV pacing leads via the coronary sinus (CS) is technically demanding, with a 10% failure rate. BiVP has not been carefully evaluated clinically as therapy for acute heart failure (ACHF).

SUMMARY OF THE INVENTION

The invention provides for a method for biventricular pacing to increase cardiac output after heart surgery in patients in heart failure. This invention is not restricted to patients in heart block, and in fact would be most frequently used in patients without heart block. Preliminary studies were performed in animals and patients with heart block for technical reasons. The invention solves the problem of implementing biventricular pacing without objective preliminary testing of how to optimize the effect of biventricular pacing. The invention provides the advantage of allowing for objective data recording; and objective, real time recording of data. This permits the correct placement and use of pacemaker devices to be customized to the patient in question, to be treated. The method of the invention comprises use of a flexible array of leads placed in a patient before cardiac bypass surgery, and/or after cardiac bypass surgery. At least 2, 3, 4, 5, 6, 7 or 8 sites can be used in any one array. The testing of the patient includes testing various site locations and various timing parameters simultaneously, in a randomized way (Monte Carlo randomization). The data can then be displayed using surface response methodology. The array will include a switching device which allows the array and the method using the array to test all locations. The invention provides methods to optimize biventricular pacing which comprises utilizing an endocardial approach for permanent placement.

In one embodiment of the invention, data are obtained in randomized order from multiple sites (in a multielectrode array). The invention provides for automated or mechanical site selection, rapid execution of a complex protocol employing multiple pacing sites. The invention also provides for adaptability to multiple anatomic configurations, adaptability to minimally invasive surgery. In one example, the device of the invention will identify the pacing lead location, where the critical lead location is an LV site (LVPS) close to the latest point of ventricular activation. Multiple leads are contemplated in the device. However, multiple LVPS testing can be impractical with temporary wires. Roving leads are slow, imprecise, and may cause mechanical effects. This invention provides for use of multielectrode bipolar leads in the posterior pericardium and electronic switching which would alleviate the problems with roving leads.

The invention provides a device (or system) capable of continuously changing heart rate (HR), atrio-ventricle delay (AVD), right-left delay (RLD), and VPS. The system of the invention includes a computer that runs programs/algorithms for rapid or automated optimization. The invention also provides for a system comprising one or more of the following components:

1. A flexible multielectrode grid of electrodes or leads. This grid is placed in the posterior pericardium when used on a subject. The electrodes are wires that provide an excitation and may also encompass wires or leads that record emission of a signal.

2. An aortic flow probe.

3. A computer program (A), generating a randomized sequence of pacing sites (VPS), right ventricular-left ventricular delays (RLDs), heart rates (HR) and atrioventricular delays (AVDs) for optimization.

4. Temporary right atrial (RA) and right ventricular (RV) wires.

5. Computer program (B), that automatically implements the randomized sequence of VPS/RLD/HR/AVD combinations while recording aortic flow.

6. Computer program (C) that selects the parameter combination producing the highest cardiac output.

7. A biventricular pacing system used for temporary pacing and controlled by program #2 (such a system is available commercially).

8. A multiplexing switch controlled by computer program B to automatically select the desired VPS in the pericardial electrode array 9. A display of the results that allows the operator to make rational decisions about what parameter combination to use for permanent pacing.

10. Range of HR is 60-100 bpm

11. Range of AVD is 90-300 msec

12. Range of RLD is −80 to +80 msec

13. Range of VPS is 6 sites on the posterior and lateral LV

14. The device would be used in an anesthetized patient or subject. Grid (1) would be positioned in the posterior pericardium and connected to the multiplexing switch (8). The switch would be connected to the computer (5) and to the biventricular pacemaker (7). The RA and RV leads (4) would be connected to the pacemaker. The range of parameters desired would be entered into the computer (3). The computer (5) would automatically execute the protocol by controlling the parameters of the biventricular pacemaker (7) and the multiplexing switch (8). Aortic flow velocity (2) would be integrated to calculate cardiac output in real time. Optimized cardiac outputs would be calculated and displayed on surface plots (9) and as a function of parameter inputs (9) allowing selection of parameters for permanent pacing. The apparatus would then be removed and permanent leads and biventricular pacemaker would be implanted and programmed.

The subject on which the method is employed may be any mammal, e.g. a human, mouse, cow, pig, dog, cat, or monkey. In one embodiment, the subject or patient is suffering from congestive heart failure, from heart failure, and/or from heart failure in surgery.

The invention presented herein solves the problem that the individual patient often doesn't see any benefit to biventricular pacing—about 30% of the patients sec no effect. Optimization of the parameters in a patient permits a patient to receive the optimal location, pacing, lead position, capture thresholds, heart rate, atrioventricular delays, left ventricular delays. For example, patients will differ as to their extent of vascularization, and these differences can be accounted for in this optimization method, resulting in the best lead position and delay and excitation parameters, etc. for that particular patient. In another example, a patient may be unique in his or her ionization state. In another example, the patient has an amount of scar tissue in the posterior pericardium. In another embodiment, a flow probe is used. The invention provided allows for rapid testing of a large number of related variables. In one embodiment, the system or apparatus has an adjustable right-left delay. In one embodiment, this system can be used for temporary biventricular pacing after surgery. This invention provides a method to optimize cardiac output in a patient with heart failure after heart surgery. The invention provides a system to test variable right-left ventricle stimulation delays.

This invention provides a system with an ability to pace over an infinite range of heart rates, atrioventricular delays, and right-left delays. Furthermore, this scanning can be done continuously and automatically, using FDA approved temporary pacemakers as the interface to the patient. In one embodiment, the invention provides an improvement over other systems based on incrementally varying critical delays. In particular, in this embodiment, this invention provides optimization of parameters based on data derived from continuous variation to derive "graphs" which are then used to select automatically the optimum settings for a particular subject. This invention provides for a system that rapidly and automatically scans a range of heart rates, atrioventricular delays and/or right-left delays while cardiac output and other data are recorded. The range of heart rate, atrioventricular delays and right-left delays tested is programmable. In one embodiment, desired values of the other parameters are programmed to fixed values during testing. In one embodiment, the system includes a pacemaker for bipolar sensing and pacing of right atrium, right ventricle, and left ventricle. The following parameters are adjustable in this invention:

heart rate from about 40 to about 150;

atrioventricular delay from about 40 to about 300 msec;

2.5 right-left delay from about 80, about 60, about 40, about 20, about 0, about −20, about −40, about −60, about −80 msec;

atrial sensitivity from about 0.15 to about 5.0 mv;

ventricular sensitivity from about 050 to about 10.0 mv; and/or output, all channels, from about 0.50 to about 10.0 volts.

Optimized BiVP is most valuable immediately after CPB when cardiac function is acutely depressed. This is also a time of relative instability, with intrinsic and iatrogenic changes in contractility, HR, intravascular volume, and vascular resistance. In certain examples of use of the device of the invention, testing intervals were at about 10 seconds. Testing 13 AVDs, 3 VPS (RV, LV, BiVP), and 9 RLDs required 360 seconds, increasing to 450 seconds with three 30 second tests of POPT vs. NoP. Some protocols ignore multiple LVPS. This problem can be alleviated by automated, rapid variation of HR, AVD, RLD, or LVPS. The computerized pacing system of the invention allows automated testing of large data sets, rapid or continuous variation of parameters, and simultaneous variation of more than one variable. Use of design of experiments (DOE) theory can define the minimum data set required. Data analysis includes RLD-CO relations, wall motion by 2-DE/tissue doppler, and synchrony of RV-LV pressure generation by micromanometer.

The invention takes advantage of the discovery of a correlation between certain pacing parameters and the optimized treatment option for a particular patient. In this method, based on the correlation, the pacing parameters, such as the (RLD) parameter, are optimized for the perioperative cardiac patient. The system uses temporary pacemakers connected to the heart and a recorder, which registers values for a patient's heart rate (HR), AVD, RLD, and cardiac output (CO). One skilled in the art will recognize that a recorder may be a computer.

The invention provides methods for clinical optimization of biventricular pacing for heart failure. For example, the method can be used for patients suffering from congestive heart failure. Although there are computer programs for pacemakers, this invention combines several programs together with the array of electrodes to form a system useful for the optimization of biventricular pacing. The system of the invention is fully automatic, randomized and incorporates full range of programmable functions. The system is advantageous because it is self-contained, automatic and computerized.

In one embodiment, the electrodes used in the methods of the invention are flexible and/or collapsible. In another embodiment, the electrodes, and/or the pacing unit are able to be introduced via a scope, port, through a small incision. For example, the electrodes can be introduced via an endoscope.

Epicardial optimization of biventricular pacing requires rapid selection of multiple alternative pacing sites. Site switching typically occurs as often as about 54 times in about 15 minutes, evaluating about 6-12 pacing sites. The invention provides for a multiplexing switch that can rapidly select the appropriate site at the appropriate time. The design incorporates both computerized selection for an automated system and a mechanical rotary switch in the event of computer failure or delays by regulatory agencies in approval of computer driven switching for use in humans. In one embodiment, the switch includes twelve terminals for connection to pacing sites by appropriate cables. Each site is bipolar, utilizing two contacts. There is a bipolar external connection to a source of regulated electrical power. A labeled rotary switch allows manual selection of the appropriate site. In one embodiment, for computer control, an electronic circuit selects the appropriate current path using a cable connected to an external computer system. The device of the invention is used to collect data in randomized order from multiple sites. The configuration assures that the same site is being evaluated for each data point. The configuration is adaptable to hearts of variable size and shape. Modification allows introduction for minimally invasive surgery. The invention provides the following advantages: automated or mechanical site selection, rapid execution of complex protocol employing multiple pacing sites, adaptability to multiple anatomic configurations, and/or adaptable to minimally invasive surgery (e.g., since the device is collapsible).

The present invention relates to a system and method for the temporary perioperative atrial and biventricular pacing in a patient with heart failure after open-heart surgery. The invention takes advantage of the discovery of a correlation between certain pacing parameters and the optimized treatment option for a particular patient. In this method, based on the correlation, the pacing parameters, such as the right left delay (RLD) parameter, are optimized for the perioperative cardiac patient. The system uses temporary pacemakers connected to the heart and a recorder which registers values for a patients heart rate (HR), atrioventricular delay (AVD), RLD, and cardiac output. In one embodiment, the system of the invention utilizes two pacemakers, and in another embodiment, the system of the invention utilizes three pacemakers. Methods for overdrive pacing and atrial pacing are provided. For overdrive pacing, the system triggers the temporary pacemakers so that the heart operates over a range of one of the variables (HR, AVD, or RLD) and records values for the other two variables. The same is performed for each of the variables. For atrial pacing the system uses the patient's intrinsic heart rate to determine the optimum AVD and RLD in a similar fashion. The present invention is not limited to left ventricular pacing. The optimum values may then be programmed into a pacemaker. One advantage over prior systems is that the speed by which this system determines the optimum values. The present invention provides a system comprising two or three pacemakers which is capable of performing multi-chamber and/or multi-site pacing. In one embodiment, the present invention uses three parameters, HR, AVD, and RLD, instead of one or two parameters.

The present invention provides systems and methods for the temporary perioperative atrial and biventricular pacing in a patient with heart failure after open-heart surgery. The discovery is that there is a correlation between certain pacing parameters and the underlying cause of the heart failure. Based on the correlation, the pacing parameters, such as the right left delay (RLD) parameter, will be optimized for the perioperative cardiac patient. The system uses temporary pacemakers connected to the heart and a recorder which registers values for a patients heart rate (HR), atrioventricular delay (AVD), RLD, and cardiac output. In one embodiment, the system of the invention utilizes two pacemakers, and in another embodiment, the system of the invention utilizes three pacemakers. Methods for overdrive pacing and atrial pacing are provided. For overdrive pacing, the system triggers the temporary pacemakers so that the heart operates over a range of one of the variables (HR, AVD, or RLD) and records values for the other two variables. The same is performed for each of the variables. For atrial pacing the system uses the patient's intrinsic heart rate to determine the optimum AVD and RLD in a similar fashion. The optimum values may then be programmed into a pacemaker. The reported advantage over prior systems is that the speed by which this system determines the optimum values.

In one embodiment, the present invention provides a system and method for the temporary perioperative atrial and biventricular pacing in a patient with heart failure after open-heart surgery. In one embodiment, the system of the invention utilizes two pacemakers, and in another embodiment, the system of the invention utilizes three pacemakers. In one embodiment, the pacemaker is a dual-chamber external (temporary) pulse generator (Medtronic 5388) and has been approved by the FDA. The pacemaker can have an atrial channel and a ventricular channel, with sensitivity adjusted in mV and pacing output adjusted in volts or milliamps.

In an embodiment in the two-pacemaker system, one end of temporal bipolar epicardial wires are attached to the right atrium (RA), right ventricule (RV) and left ventricule (LV) of the heart. The other end of the atrial wires are attached to the atrial channel of the pacemaker and the other end of the ventricular wires are attached to the ventricular channel of the pacemaker. A computer may be incorporated into the system to create a closed-loop control system. To accomplish the objective of the two-pacemaker system, the RA and RV wires are attached to the RV pacemaker and the RA and LV wires are attached to the LV pacemaker. Prior to pacing, the RA, RV and LV wires are tested to confirm reliable pacing of the chamber to which they are connected.

In the two-pacemaker system, the critical pacing parameters are the heart rate (HR), the atrioventricular (AV) delay and the right-left delay (RLD). Prior to pacing, the pacemaker is adjusted to atrial-triggered ventricular demand pacing ("DDD" pacing). In DDD pacing, the HR determines a minimum acceptable atrial rate. For example, if the rate of the atrium falls below this value, the pacemaker paces the atrium at the lower rate limit. Whether the ventricule is paced is determined by the AV delay. AV delay timing is started by atrial pacing or a spontaneous atrial depolarization. If the programmed AV delay expires with no ventricular depolarization detected the pacemaker paces the ventricle.

The two-pacemaker system allows optimization of the AV delay by manual adjustment of the AV delay over a time range. Following AV delay optimization, the RLD can be optimized. This can be accomplished by use of an algorithm simulating the RV or LV pacemaker, or by use of reference tables which show the value of AV delay needed for each RV or LV pacemaker. The algorithms can be incorporated into the computer or into the pacemaker. The parameters may be optimized manually by adjusting the pacemaker or automatically with the computer or pacemaker.

The two-pacemaker system allows the pacing of the RA by the RV pacemaker which would begin the timing of the AV delay in both pacemakers. The pacemaker with the shorter AV delay would pace the ventricle to which it is connected. The second pacemaker would be paced second, after the appropriate RLD. One benefit of the two-pacemaker system is that by using an algorithm or correlation between the pacing parameters and the underlying causes of the heart failure necessitating the cardiac operation, the pacing parameters can be optimized for the perioperative cardiac patient.

In the three-pacemaker system embodiment of the invention, the critical pacing parameters are the heart rate (HR), the atrioventricular (AV) delay and the right-left delay (RLD). All three pacing parameters can be computer optimized via various computer-driven algorithms. The right channel of the computer is connected to the atrial channel of the first and second pacemakers, and the left channel of the computer is connected to the atrial channel of the third pacemaker. Temporary bipolar pacing wires are used for connection to the heart via attachment between the ventricular channel of the first pacemaker and the right atrium, the ventricular channel of the second pacemaker and the right ventricle and the ventricular channel of the third pacemaker and the left ventricle. For each pacemaker, the AV delay between the atrial channel and the ventricular channel can be adjusted. A recorder registers flow velocity from an ultrasonic flow probe on the ascending aorta, registers the electrocardiogram, and signals from the atrial, right and left channels of the computer.

In one embodiment of the invention, all three pacing parameters can be varied by entering the desired HR, AV delay and RLD into the computer. When HR is varied, the computer is programmed with a desired range of FIR and a desired AV delay and RLD. The computer transmits a triggering signal to the first pacemaker, which sense the right atrium at the desired rate. Triggering signals are sent to the atrial channel of the second and third pacemakers after delay to trigger RV and LV pacing. The entire range of HR is tested with varying FIR. When AV delay is varied, the desired range of AV delay, HR and RLD is programmed. The computer triggers all three pacemakers in the correct sequence to cover the range of AV delays. When RLD is varied, the desired range of RLD, HR and AV delay is programmed. The computer triggers all three pacemakers in the correct sequence to cover the range of RLD's. The three-pacemaker system thus provides a closed-loop of the pacing parameters to achieve optimum heart function. In one embodiment, a benefit of the three-pacemaker system allows a predetermined series of pacing parameters to be tested automatically and optimized. Another benefit is that the correlations between the pacing parameters and the underlying causes of heart failure allows for optimization of pacing parameters for a perioperative cardiac patient.

The invention provides for a computerized switch for epicardial pacing optimization and an electrode array. Epicardial optimization of biventricular pacing requires rapid selection of multiple alternative pacing sites. Further, this invention provides a method to determine optimum site selection using a quadratic response comparing cardiac output (CO) against atrio ventricular delay (AVD) or right ventricular to left ventricular delay (RLD).

The patent and scientific literature referred to herein establishes knowledge that is available to those with skill in the art. The issued patents, applications, and other publications that are cited herein are hereby incorporated by reference to the same extent as if each was specifically and individually indicated to be incorporated by reference. In the case of inconsistencies, the present disclosure will prevail.

BRIEF DESCRIPTION OF THE FIGURES

FIG. 5B illustrates cardiac output data for only 15 of these AVD-RLD combinations modeled by a quadratic response surface model. Darkest areas of highest CO indicate ranges of AVD (vertical axis) and RLD (horizontal axis) that direct the POPT. Lighter areas indicate those areas to be avoided for permanent placement of pacemaker leads.

DETAILED DESCRIPTION OF THE INVENTION

Figure 1:
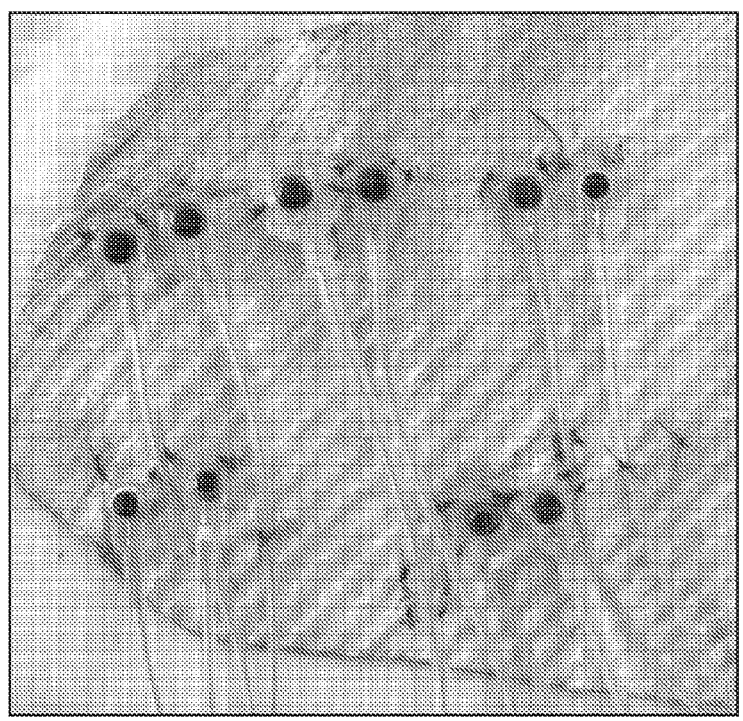
FIG. 1. is photograph of a prototype of five bipolar electrode array.

A description of methods for cardiac resynchronization therapy and biventricular pacing can be found in U.S. Pat. No. 6,978,184, issued on Dec. 20, 2005 is hereby incorporated by reference in its entirety.

Optimized BiVP is a valuable adjunct to the treatment of LVD, RV dysfunction (RVD) or acute heart failure (ACHF) after cardiac surgery (OHS) for acquired (AHD) or congenital (CHD) heart disease. Accumulating data suggests that algorithms for an optimum pacing protocol (POPT) will not be stable over time, and that an automatic, self-optimizing BiVP system will provide greater clinical benefit than fixed algorithms. In one embodiment of the invention, the following steps are used to implement a self-optimizing clinical system:

1. One can determine the influence of the effects of positive inotropes, vasodilators and vasoconstrictors on POPT. Such factors can be tested in models (such as an animal model) of ACHF with RVD and LVD.

2. Algorithms using continuous variation in HR, AVD, and RLD for BIVP OPTZN can be used, and can be validated in animal models of ACHF with RVD and LVD. UFP CO can be used for monitoring.

3. An automated device incorporating validated algorithms can be used.

4. An automated device incorporating clinically useful monitoring technology can be used and can be confirmed in animal models of ACHF with RVD and LVD prior to clinical trials in patients.

Vasoactive Agents in Severe PS and HB:

Effects of dopamine, sodium nitroprusside, and neosynephrine on AVD-CO and RLD-CO relations can be tested in the model of severe PS. Data Analysis: AVD-CO and RLD-CO relations will be analyzed by MMM. Differences in OPT RLD and AVD for the four conditions examined will be tested for significance by ANOVA.

BIVP OPTZN using continuous variation of HR, AVD, and RLD over time will be compared to results of stepwise testing over 10 second or 30 second intervals in severe PS and the control state. HR, AVD, and RLD can be varied over a wide range and in very small increments with a computer controlled system. Commercial 5388s are used for sensing and pacing signal generation, but the computer determines timing. HR, AVD, and RLD are tested and assessed individually and sequentially. However, more complex logic could optimize all simultaneously. In one embodiment, pacing determinants are continuously increased or decreased during testing. With HR, the range of interest can be from about 70 to about 100 bpm. The interval between changes in HR can be based on an integral number of beats and can include an adjustment for time (e.g. two beats at a HR of about 120 would be equivalent to one at a HR of about 60). If the computer increases HR one bpm after each beat, it will take roughly 25 seconds to increase HR from 70 to 100 and another 25 to reduce HR back to 70. This sequence would be repeated three times to assess reproducibility. Similar approaches would be used for AVD and HR.

LVPS and RLD Optimization During Rapid and Standard Measurements.

In one embodiment, a standard preparation will be modified with jet ventilation, MVO2 determination, and, from R1/L1, a multisite electrode in the posterior pericardium and computer controlled pacing. Computer control is needed to provide automated algorithms or multisite VPS testing. HR will be about 90, and AVD will be about 120 msec. RLD-CO relations will be measured during BiVP at a single RV site and each of six LVPS using both 30 second testing intervals and rapid programming during jet ventilation. The initial rapid testing algorithm will use three second testing increments, exploring the full range of nine RLD values, −80 to +80 msec, in 27 seconds. This range will be scanned again in reverse order for a total of 54 seconds of testing. Results will be digitized, averaged, and displayed in real time. This scheme allows all RLD-CO data for 6 LVPS to be derived in less than 6 minutes.

Automated Pacing:

Automated pacing can be accomplished by a computer-based system driving temporary dual-chamber pacemakers. LabVIEW (National Instruments), an open environment for signal acquisition, measurement analysis, and data presentation, will be interfaced with three Medtronic 5388 temporary pacemakers via a PCI board. The PCI board allows electrical signals to be sent and received by the computer. This will allow LabVIEW to send and receive voltage signals to and from the pacemakers. During overdrive pacing, LabVIEW will send an output signal to trigger the atrial channel of the RA pacemaker. The ventricular pacemakers will always be triggered by LabVIEW output pulses to their atrial channels. Algorithms written in LabVIEW will be implemented to control the timing of the output pulses in order to set the desired AVD, RLD and HR via the pacemakers. The LVPS will be controlled by LabVIEW with a switch between the electrode patch and the LV pacemaker. In this way, algorithms can be written in to automatically run through desired protocols. This will allow complete computer control of the order and magnitude of pacing settings, AVD, RLD, LVPS and HR, as well as the duration of pacing intervals. For self-optimization, the CO signal from the flow probe will be received by LabVIEW and analyzed to determine optimum settings.

DOE and Response Surface Methodology:

In contrast, DOE offers an organized approach that connects experiments in a rational manner, giving more precise information from fewer experiments. Factorial experimental design investigates all possible combinations of the levels of the factors. It is more efficient than one-factor-at-a-time experimentation, is necessary when interactions may be present to avoid misleading conclusions, and allows the effects of a factor to be estimated at several levels of the other factors, yielding conclusions that are valid over a range of experimental conditions. One useful output of DOE is a response surface map (RSM) of the experimental region. RSM is a collection of mathematical and statistical techniques for analyzing the influence of several independent variables on a dependent variable. The goal is to optimize the response. RSM begins with definition of a suitable approximation for the true functional relationship between the response and the set of independent variables. Consider CO as a polynomial function of two inputs, AVD and RLD. The function CO=f(AVD,RLD) describes a two-dimensional surface in space (AVD,RLD,CO). In general, the number of input variables is unlimited, and the resulting surface becomes a hypersurface. From our experience, the shapes of our 1-dimensional CO response curves (an example being the RLD-CO relation) are generally quadratic and smooth, with a relatively broad peak, so the curves may be reasonably approximated by a quadratic polynomial. Thus, in 2-dimensions, the surface may be approximated by a quadratic response surface model and the approximate location of the peak can be rapidly established with a relatively small number of measurements:

$$CO = c0 + c1(AVD) + c2(RLD) + c3(AVD)(RLD) + c4(AVD)2 + c5(RLD)2$$

This was implemented in Matlab. Even if additional measurements are used to refine the initial estimate of POPT, the total optimization time can be reduced by approximately half.

Ventricular Synchrony in BiVP:

Benefit of BiVP in DCM is attributed to improved ventricular mechanics and resynchronization of contraction. Mechanical interventricular asynchrony can be estimated by two measures. (1) The time delay between the upslope of the normalized RV and LV pressure signals calculated by shifting the upslope of normalized RV and LV pressure in time until the cross-correlation coefficient between the two signals reaches a maximum. The time shift gives the delay between the signals. Useful data is restricted to the contraction phase. (2) The area of the normalized RV-LV pressure diagram calculated from a plot of normalized LV-RV pressure. The principle is that identically shaped signals plotted against each other produce a loop area of zero if the signals are completely synchronous, increasing towards one with increasing asynchrony. Pressure is plotted over the complete cardiac cycle. Both indices are positive for earlier LV than RV pressure and equal to zero for mechanical synchrony.

Data Analysis:

Average HR-CO relations would be determined for increasing HR, AVD, and RLD vs. time. The decreasing limbs and overall average relations would also be calculated. Accuracy of derived algorithms and time to accomplish OPTZN will be compared for continuous and stepwise OPTZN. Utility of UFP, PulseCO, O2sat, and MAP will be compared, as a guide to clinical studies. Results will define advantages of continuous vs. stepwise analysis in an automated system.

Self-Optimizing BiVP in Severe PS and HB:

The algorithms developed above can then be employed in BiVP. UFP feedback loop will allow the pacing system to assess the relation of CO to critical pacing variables over time and adjust those variable accordingly. PS, PS+dopamine, and control states would be tested. The algorithm will explore from the center of a range of interest and will not explore extreme values if CO decreases more than 10%.

Invasive Monitoring for Clinical BiVP:

In its current form, UFP based CO is not practical for a clinical system. Appealing alternatives include O2sat, PulseCO, flow velocity catheters, and new technologies. RHBP is a gold standard for assessing accuracy of aortic flow measurement because flow is known and can be varied with extreme accuracy. RHBP can be used in these methods. Linear regression will be used to correlate true aortic flow with measured data.

Noninvasive Monitoring for Clinical BiVP:

Noninvasive measures of CFN, including SV will be tested by echo Doppler, tissue Doppler, thoracic impedance, oximetry, and others. The subjects in this embodiment can be closed chest pigs under general anesthesia will be used. CO, measured by lithium calibrated PulseCO and thermal dilution CO (SG), will be altered with DRIPS as in L1. HR will be altered by transesophageal pacing. Linear regression will compare PulseCO and thermal dilution CO to candidate technologies.

Self-Optimizing Clinical BiVP in Severe PS and HB:

In this embodiment, the algorithms developed in the above methods and in the self optimizing system will be combined with clinical monitoring technology in a prototype clinical system.

Basic Preparation:

Domestic pigs (40-50 kg male) are anesthetized with ketamine hydrochloride (20 mg/kg IM), xylazine (4 mg/kg IM), and atropine sulfate (1-2 mg IM). Following intubation, anesthesia is maintained by mechanical ventilation with 1-1.5% isofluorane and oxygen. Body temperature is maintained with a heating pad. Normal saline (0.9%) is infused via ear vein at 10 mL/kg/hr for the first hour, 5 mL/kg/hr thereafter. Monitoring includes arterial blood gases, ECG, and femoral artery pressure, (fluid filled catheter/transducer; model 7758, 8-channel recording system; Hewlett-Packard, Andover, Mass.).

Following median sternotomy, insertion of a sternal retractor and longitudinal pericardiotomy, the AAo root and main PA are dissected free and encircled with umbilical tapes.

Instrumentation:

A pericardial well is created for Q2-DE by sewing a polyethylene bag to the pericardium and draping the free edges over the opened sternum. A 16 mm A-series transit time UFP (Transonic Systems Inc., Ithaca, N.Y.) filled with acoustic coupling gel is placed around the AAo and connected to a dual channel flowmeter (HT207, Transonic). After systemic heparinization (100 U/kg), a 5 segment, 6 Fr., dual field combination COND and micromanometer catheter (Millar Instruments, Houston Tex.) is inserted through a purse-string suture in the LV apex. This is connected to a signal conditioner (Leycom Sigma-5 COND module, Rijnsburg, Netherlands). The Leycom Sigma 5 also measures COND and blood resistivity (p) via a 6 ml. Rho cuvette. The position of the COND catheter is verified by 2-DE in the standard apical LV long-axis position, to assure that contact of the electrodes with the endocardium is avoided. 2-DE also aids positioning the two distal current setting electrodes (20 KHz, 30 mA) across the aortic valve and the five pairs of intervening electrodes measuring voltage drops in the LV chamber. Electrode segment location is also confirmed by plotting the LV PV loop for each segment on a digital oscilloscope. Clockwise loops originate from the AAo, counterclockwise loops from the LV. The COND catheter position is satisfactory when all segments produce counterclockwise PV loops. An RV combination catheter is inserted similarly, from the RA to the RV apex. Segments that do not cross the tricuspid valve are electrically excluded from summated COND. A thin rubber membrane (Speedo Swim Gear) is placed in the posterior pericardium as a COND insulator. An occlusive cardioplegia catheter is inserted from the RA to the CS for collection of samples and flow measurement.

Micromanometer:

Micromanometers are pre-soaked in sterile saline for 30 minutes prior to calibration. Pressure calibration is done with a column of normal saline in a graduated cylinder. 0 mmHg is recorded as the pressure sensor is placed just below the surface. 10 mmHg is recorded 13.6 cm below the surface. LVEDP: LV pressure coincident with the R wave of the ECG.

Initial Pacing and HB:

Bipolar temporary epicardial pacemaker leads are sewn to the RA, RV, and LV. The leads are attached to an InSync III temporary pacing box. After BL data recording and validation of sensing and pacing, the AV node is ablated. Ethanol (100%) in 0.05 ml increments is injected into the AV node/His bundle along the medial aspect of the tricuspid annulus, confirmed by direct palpation through an RA pursestring. The ECG is monitored until 3° HB develops. The RV and LV are paced initially at an AVD of 150 msec, tracking the RA rate. The subject is monitored to confirm hemodynamic stability.

Pressure Overloads:

Severe PS: A PA snare is tightened until peak RV systolic pressure doubles.

AS:

An AAo supracoronary snare is tightened until peak LV systolic pressure doubles.

Volume Overloads:

For each of the following, retrograde flow is monitored by UFP and adjusted with a snare.

TI:

An aortic allograft with plastic cannula tips is placed through pursestring sutures from RA to RV.

MR:

An aortic allograft with plastic cannula tips is placed through pursestring sutures from LV to LA.

AI:

An aortic allograft with plastic cannula tips is placed through pursestring sutures from AAo to LV.

Hemodynamic Data:

Analog data are digitized at 200 Hz (MacLab A/D converter) and stored on a Macintosh G4 Powerbook computer, with data archives on writable CDs. IGOR or MacLAB software written for this purpose allows calculation of standard indices of systolic and diastolic function.

COND is calibrated by comparing SV by COND and UFP to calculate alpha (152). Parallel COND is then derived, from Q2-DE measurement of RVEDV or LVEDV (152).

RHBP:

A lidocaine bolus 2-4 mg/kg is administered, followed by a lidocaine drip at 50 mcg/kg/min. The subject is heparinized with 300 IU/kg IV. A two-stage 28 Fr venous cannula is inserted in the RA via a 4.0 Prolene pursestring suture. A metal-tip arterial cannula is inserted in the LA via a 4.0 Prolene pursestring. A suction vent is inserted into PA via 4.0 Prolene purse-string suture. CPB is begun at 2 L/min, lungs are deflated. Pancuronium (0.02-0.15 mg/kg IV) is administered. Pentothal 10-30 mg/kg is given IV as needed.

RHBP Interventions:

Decrease flow from 3 L to 1 L in 0.5 L steps, with stabilization intervals of 10, 30, and 60 seconds, then reverse the steps. RA pacing at intrinsic rate and NP for 30 second periods at flows of 3.0 and 2.0 L/min.

Vasoactive Drips for Animal Studies:

Phenylephrine (Neosynephrine) 1-2 mcg/min, titrate to 20% increase in MAP. Sodium Nitroprusside (Nipride) 0.5-1.0 mcg/kg/min, titrate to 20% decrease in MAP. Dopamine 5 mcg/kg/min. Clamp femoral artery distal to arterial line to change arterial COMP.

Sonomicrometry:

Equatorial sonomicrometry is used to measure short axis segment length. One pair of 0.5 cm bidirectional piezoelectric crystals (Sonometrics, Inc., London ON Canada) is placed circumferentially at the maximum LV diameter and secured to the epicardium with 5-0 prolene sutures. Crystal signals are enhanced with an oscilloscope and digitized. Data are compared to Q2-DE.

MVO2:

In humans, MVO2 will be measured as the product of the difference in coronary artery O2sat and CS O2sat ($\Delta$AVO2) determined by hemoximeter and coronary flow measured by an intracoronary Doppler catheter placed in the proximal left main coronary artery. This assumes that flow velocity is proportional to volume of flow, which is the case if vessel diameter is constant. Experimentally MVO2 will be measured using the same formula, but a UFP will be placed around the left main coronary artery to determine flow. The PI is experienced with MVO2 measurements.

Statistical Methods:

For simple designs, with paired data, (i.e. pre and post-op data) a paired t-test will be utilized. For comparison of two independent groups, the standard student's test will be employed; for three or more groups, ANOVA. If we find significance among these groups, a multiple comparison procedure such as the Scheffe test or Tukey's test for pairwise differences will be employed to discern where the differences lie. These methods also control for the potential increase in the Type I error associated with multiple testing. To correct for possible difference in baseline measurements, ANCOVA is the method of choice. This offers adjusted group means, correcting for group differences at baseline. The homogeneity of slope assumption will be tested. If there are repeated measures over time per individual, MMM (Proc MIXED, The SAS System software, SAS Institute, Inc., Cary, N.C.) will be the chosen procedure. This approach estimates the standard errors by modeling the covariance structure of the repeated measures. These measures are inherently correlated within subject. Three of the more common covariance structures include "compound symmetry" for correlations that are constant for any two points in time, "auto-regressive order one" for correlations that are smaller for time points further apart, and "unstructured", which has no mathematical pattern within the covariance matrix. Other covariance structures that will be tested include the Toplitz and the Heterogeneous Compound Symmetry structure. For other independent continuous outcome data, which may be correlated to a number of factors, ordinary least squares linear regression techniques will be utilized. Time-dependent outcome variables may be analyzed using Kaplan-Meier Product-limit estimating techniques.

2-DE is acquired with a GE/Vingmed CFM 800 or General Electric Vivid 7 Vantage Release (GE Medical, Milwaukee, Wis.), using a hand-held epicardial 5.0 or 7.5 MHz ultrasound transducer and scanning gel (Ultraphonic scanning gel, Pharmaceutical Innovations, Inc. Newark N.J.) to provide a standoff between the epicardium and the transducer. Using the General Electric Vivid 7 Vantage Release System, LV short axis 2-D images with simultaneous tissue Doppler imaging (in background) are acquired. Imaging frame rate, including tissue Doppler, will exceed 115 fps. The system allows unlimited 30-second capture and storage of digital cineloops. In addition to the 2-DE, time (msec), gain, and offset controlled electrocardiogram is also included in the digitized cineloop. The stored tissue Doppler information will allow strain, SRI, and displacement (Tissue Tracking) to be processed and displayed in qualitative velocity color maps or as quantitative wave forms. For functional comparisons, 2-DE is digitized and videotaped under all conditions of interest. 2-DE data are digitized to calculate LV EDA, ESA, EF, eccentricity, and WMA.

2-DE LV models include Simpson's rule algorithms (stacked ellipsoids) and ellipsoids of revolution. In experimental animals, algorithms have been validated against postmortem PV curves and volume of postmortem casts of LVs fixed at the LVEDP observed in vivo. Current procedure involves 4-chamber (0°), 2-chamber (62°) and long axis (101°) views traced and reassembled into a Cartesian xyz system. Sixteen stacked disks are constructed with cubic splines and the endocardial surface is reconstructed from multiple interpolated apical and cross-sectional borders.

Q2-DE Calculations. LVEDA:

The largest short axis cross section during the cardiac cycle at the midventricular level, generally close in time to the R wave of the ECG. All echo measurements in the steady state are done by averaging results in three separate beats.

LVESA:

The smallest short axis cross section at the level and sectioning plane used for LVEDA. Increased LVESA after CPB can indicate LVD.

EF:

Equals 100*(EDA−ESA)/EDA. Increases with EDA or contractility, inversely related to SYR.

LVM:

Calculations are based on three long axis sections (apical long axis, two chamber, and four chamber views). Mass is given by the calculated wall volume (epicardial volume minus endocardial) multiplied by 1.055, the specific gravity of myocardium. In LV short axis cross sections, the epicardium and endocardium define the myocardial ring. Ring area can be converted to LVM based on our previously defined validation equations. LV Eccentricity: Ratio of perpendicular minor semiaxes bisecting the IVS (D1) and the papillary muscles (D2). D1/D2 at midventricle calculates eccentricity.

Segmental WMA:

Matlab routines facilitate analysis of global and local LV function. The endocardial borders of digitized end-diastolic and end-systolic short-axis 2-DE LV images are delineated. This is done with manual planimetry by an investigator blinded to the experimental conditions, following American Society of Echocardiography standards. This provides global measures of LV function including EDA, ESA, SA and EFa. The borders are superimposed by alignment of "floating" centroids. Using a modified Fourier analysis technique described by Kass et al., points are interpolated at 100 evenly spaced locations around the border for regional analysis. Radial chords are generated from the centroid to these points, giving radial dimensions of the LV and allowing investigation of regional shape. By measuring the change in length of the chords between time points we get a measure of local wall motion. Regional fractional shortening is calculated by dividing the change in chord length by the initial length. By tracing the epicardial borders, measures of local wall thickness are obtained (the difference between epicardial and endocardial chord lengths) also permitting calculation of fractional wall thickening. Local fractional shortening and wall thickening provide an index of regional LV systolic function. Local curvature can be measured by differentiating the Fourier series. Combined with pressure data, curvature can be used to estimate local circumferential LV wall stress. Measures of regional curvature and wall stress compliment measures of regional shape, fractional shortening and wall thickening, which are reference system dependent, since they describe an intrinsic regional property of the LV that is independent of any external or internal reference system Computer Driven TPCP:

Until recently, TPCP was controlled by manual adjustment of HR and AVDs on two 5388 temporary pacemakers. A computer driven system that can automatically run defined protocols is useful in these methods. A third 5388 provides computer controlled RA sensing or pacing. HR is programmable. A programmable AVD sequence (e.g. 60, 90, 120, 150, 180 msec) is initiated on command. The IAD is requested and incorporated into the protocol as needed. OPT AVD is entered, once known. On command, the correct sequence of triggering impulses for AVDS and RLDs is delivered to the "A" channels of 5388R and L. High level user interface programming is done in Java running on Mac OS X on an Apple iBook. The host computer offloads timing signals to a Cypress Semiconductor EZ-USB device. This device combines a USB interface with a general purpose 8051 microprocessor. The 8051 microprocessor is programmed by downloading assembler firmware from the host computer. Extremely precise (within a few microseconds) time delays are generated using the 8051's 16 bit hardware timers. The 8051's input and output pins are interfaced via buffer amplifiers to clinical temporary pacemakers. The 8051's input and output pins are buffered by op amps which convert pacemaker voltage levels (millivolts) to chip logic levels (3.3 volts logical high). The control system is well suited to the experimental task, since it provides a convenient window based user interface with logging capabilities and also can drive low level hardware with great timing accuracy. Adaption of this system to automatic pacemaker optimization is straightforward in experimental animals, using UFP feedback.

BiVP:

FDA approved Medtronic 5388 temporary pacemakers can be used. DDD/BiVP (RLD=0) was obtained by connecting the ventricular output of a 5388 to both the RV and LV. For laboratory studies of RLD, two 5388 Medtronic dual chamber units were employed. Epicardial RA electrodes were connected to the atrial terminal of both units. The RV was connected to the ventricular terminal of one 5388, the LV to the other. AVDs on the 5388s determined RLD. To pace the RV first with an AVD of 100 msec, the AVD on the RV 5388 was set at 100 msec. If the desired RLD was 60 msec, the AVD on the LV 5388 was set at 160 msec. Blanking or reduced sensitivity prevented inhibition by RVPc. Tables defined settings for AVDs of 60 to 210 msec and RLDs from +80 (RV first) to −80 (LV first). This can also employ a computer driven system.

Pathologic Loading Groups for Analysis of TPCP Studies in Humans

A. RV Pressure Overload: Tetralogy of Fallot, Cardiac Allograft, Pulmonary Emboli
B. RV Volume Overload: TI, ASD
C. LV Volume Overload: MR, AI, VSD
D. LV Pressure Overload: AS, Systemic Hypertension
E. CAD Representative Pacing Protocols

| C-1a | AVD* | Time (sec) |
|---|---|---|
| HR=BL | 90 | 10 |
| VPS=RV | 120 | 20 |
|  | 150 | 30 |
|  | 180 | 40 |
|  | 210 | 50 |

-continued

| | | |
|---|---|---|
| | 240 | 60 |
| | 270 | 70 |
| | 240 | 80 |
| | 210 | 90 |
| | 180 | 100 |
| | 150 | 110 |
| | 120 | 120 |
| | 90 | 130 |

| C-1b | VPS | Time(sec)** |
|---|---|---|
| HR=BL | RV# | 140 340 |
| LV# | 150 | 330 |
| BiV+80 | 160 | 320 |
| BiV+60 | 170 | 310 |
| BiV+40 | 180 | 300 |
| BiV+20 | 190 | 290 |
| BiV+0 | 200 | 280 |
| BiV−20 | 210 | 270 |
| BiV−40 | 220 | 260 |
| BiV−60 | 230 | 250 |
| BiV−80 | 240 | |

**times reflect duplication and reversal of VPS
Not applicable to protocol

Elapsed Time in Seconds

| C-1c | VPS | Time (sec) |
|---|---|---|
| HR=BL | OPT | 370 |
| AVD=OPT | BL | 400 |
| RLD=OPT | OPT | 430 |

C-1d (Supplemental AVD Testing)

| | AVD | Time (sec) |
|---|---|---|
| HR=BL | 90 | 20 |
| VPS=BiV | 120 | 40 |
| RLD=OPT | 150 | 60 |
| | 180 | 80 |
| | 210 | 100 |
| | 240 | 120 |
| | 210 | 140 |
| | 180 | 160 |
| | 150 | 180 |
| | 120 | 200 |
| | 90 | 220 |

The following examples illustrate the present invention, and are set forth to aid in the understanding of the invention, and should not be construed to limit in any way the scope of the invention as defined in the claims which follow thereafter.

EXAMPLES

Example 1

Optimized Biventricular Pacing in Atrioventricular Block after Cardiac Surgery

Temporary perioperative cardiac pacing is often required after open-heart surgery for treatment of sinus bradycardia and transient heart block. The effect of temporary perioperative cardiac pacing on cardiac output (CO) and stroke volume is rarely measured despite parameters that might be manipulated to the patient's advantage including heart rate (HR), ventricular pacing site (VPS), and atrioventricular delay (AVD). Use of ultrasonic transit-time aortic flow probes makes measurement of CO and stroke volume during implementation of temporary perioperative cardiac pacing more feasible. Atrioventricular delay and ventricular pacing site can be manipulated to increase cardiac output. By optimizing both atrioventricular delay and ventricular pacing site a 10% improvement in cardiac output would be observed compared to a standard pacing protocol. Seven patients in first or third degree heart block after valve replacement surgery had temporary wires sewn to the right atrium, right ventricle and left ventricle. Cardiac output was measured by integrating flow velocity from an ultrasonic aortic flow probe. After optimization of atrioventricular delays during atrial synchronous right ventricular pacing, the effects of ventricular pacing site were tested at the optimum atrioventricular delay for 10-second intervals.

Biventricular pacing was beneficial in all patients with a mean increase of 22% in cardiac index over right ventricular pacing (1.95 L/min/m2±0.27 SEM to 2.38 L/min/m2±0.27 SEM, p=0.0012) and 14% over left ventricular pacing (2.08 L/min/m2±0.22 SEM to 2.38 L/min/m2±0.27 SEM, p=0.0133). Comparing optimized to standard pacing for 30-second intervals yielded a mean increase of 10% in cardiac index over three respiratory cycles (2.87 L/min/m2±0.33 SEM to 2.60 L/min/m2±0.37 SEM, p=0.009) and 17% at the corresponding end-expiratory beats (2.76 L/min/m2±0.33 SEM to 2.36 L/min/m2±0.36 SEM, p=0.011).

Biventricular pacing at optimum atrioventricular delay improves cardiac output in patients with postoperative heart block by at least 10% compared to standard pacing.

Clinical trials have confirmed that simultaneous pacing of the right ventricle (RV) and left ventricle (LV) via a second pacing lead in a lateral branch of the coronary sinus can narrow the QRS complex and improve exercise capacity and quality of life, possibly leading to reduced hospitalization in patients with severe heart failure and intraventricular conduction delays. (Cazeau et al. N Eng J Med 2001; 344:873-880.) With regard to epicardial pacing, comparison of DDD and VVI modes has shown that DDD pacing improves CO at any given HR. (Raichlen et al. "The effect of the site of placement of temporary epicardial pacemakers on ventricular function in patients undergoing cardiac surgery." *Circulation* 1984; 701118-23.) Studies in experimental animals have demonstrated that DDD pacing reduces MVO2 when compared to VVI pacing. Biventricular pacing (BiVP) has been shown to be effective with epicardial leads in both right and left bundle branch block (LBBB).

The present invention optimizes temporary perioperative cardiac pacing in patients with atrioventricular block (AVB) after separation from cardiopulmonary bypass (CPB). The effect of temporary perioperative cardiac pacing optimization on CO was measured at a HR selected by a surgical team in order to show that BiVP at optimal AVD yields a 10% improvement in CO compared with standard RV pacing at optimal AVD or no pacing.

With the consent of the attending surgeon, patients undergoing open-heart surgery with a high probability of postoperative AVB were enrolled in this study. Candidates included patients undergoing valve replacement surgery and patients with known first, second or third degree block. Preoperative data were obtained by chart review and included left ventricular ejection fraction (LVEF), LV diastolic dimension from echocardiograms and PR interval, QRS duration, heart rate, and intraventricular blocks from electrocardiograms. The cardiac rhythm prior to pacing and actual surgery performed were recorded.

Prior to separation from CPB, patients with normal atrial rates had standard temporary wires sewn to the right atrial appendage, anterior RV, and obtuse margin of the LV. Lead placement was consistent in all patients. Patients were connected to a 5388 Medtronic Dual Chamber temporary pacemaker. Sensing and pacing functions of these wires were tested and confirmed. An appropriately sized real-time ultrasonic flow probe (Transonic Systems Inc., Ithaca, N.Y.) was placed on the ascending aorta. When the patient had been successfully weaned from CPB and volume loading and pressor support had been optimized, the protocol was initiated at a HR defined by the surgical team. During the period of data acquisition, there were no changes in pressor support. Data acquisition was initiated within 5 minutes following separation from CPB.

Data Acquisition:

ECG, arterial pressure and flow velocity tracings were sampled and transferred through a 16-channel analog to digital converter (PowerLab, ADInstruments Inc, Milford, Mass.) to a computer (iMac, Apple Computer, Cupertino, Calif.). During atrial and RV pacing (DDD), AVD was increased by 30 ins increments from 90 ms to 270 ms, and then decreased incrementally to 90 ms for 10-second intervals. Optimum AVD was determined by comparing CO values displayed by the flowmeter. Effects of VPS (RV, BiV, LV) were then tested at the optimum AVD for 10-second intervals. After determining the optimum VPS (OPT), pacing was then alternated between the OPT and baseline VPS (BL) for 30-second intervals. BL setting, as determined by the surgeon, was either RV pacing or no pacing. Table 1 shows the pacing protocol and elapsed time in seconds. Following data collection, instrumentation was removed and temporary perioperative cardiac pacing controlled by the clinical team.

For the 10-second intervals, CO data was obtained by integrating flow velocity tracings over paired beats at end-expiration using MacLab software (ADInstruments Inc, Milford, Mass.). For the 30-second intervals, CO data was obtained by integrating flow velocity tracings over three respiratory cycles as well as the corresponding end-expiratory beats for each of the three cycles. Using custom designed routines in MATLAB (The MathWorks, Inc., Natick, Mass.), beat-to-beat CO and mean arterial pressure (MAP) were calculated across three respiratory cycles for the OPT and BL settings. Each respiratory cycle was defined as the time between successive end-expiratory points (point of minimum MAP). The CO values from the three respiratory cycles for each setting were averaged and time expressed as percentage of the respiratory cycle. All CO data was indexed by body surface area.

Statistical Analysis:

A mixed model methodology (PROC MIXED) was used to analyze the effect of AVD on cardiac index (CI) as well as the effect of VPS on CI. To discern differences among the three sites, contrast statements were utilized. This test controls the type I comparisonwise error rate, not the experimentwise error rate. With the assumption that CI data follows a normal distribution, a paired t-test was utilized to analyze the effect of OPT and BL settings on CI. To discern whether there were differences in CI across the respiratory cycle and between BL and OPT settings, a two factor, repeated measures analysis of variance design was performed, with repeated measures analyzed for both factors, i.e. pacing setting and percentage of the respiratory cycle. In addition, a paired t-test was utilized to compare CI values at end-expiration with the mean for other time points in the respiratory cycle. All data were analyzed using SAS system software (SAS Institute Inc., Cary, N.C.).

A total of 15 patients were enrolled in this study. Eight patients were excluded because they did not develop heart block. Upon separation from CPB, the protocol was initiated in 7 patients. Six patients developed complete heart block and one patient remained in first-degree heart block. Preoperatively, 4 patients were in normal sinus rhythm and 3 patients were in first-degree heart block. LV diastolic dimensions were available in only 2 patients and were abnormal in both cases (5.8 cm, 6.7 cm). QRS duration on preoperative ECG was greater than 140 ms in 5 patients and less than 120 ms in 2 patients. Preoperative LVEF was greater than 35% in 6 patients. All patients underwent either aortic or mitral valve replacement surgery. One patient underwent both aortic and mitral valve replacement surgery. None of the patients required permanent pacemaker implantation postoperatively as complete heart block was transient.

Clinical Results:

AVD significantly affected CI for all patients (p=0.0002). Post-tests revealed significant differences in CI at AVD values of 90, 210, 240, 270. Optimum AVD was 150 ms in 3 patients, 120 ms in 2 patients, 180 ms in 1 patient, and 210 ms in 1 patient. The individual effect of VPS on CI for all patients is shown. At optimum AVD, BiVP was beneficial in all patients with a mean increase in CI of 22% over RV pacing (1.95 L/min/m2±0.27 SEM to 2.38 L/min/m2±0.27 SEM, p=0.0012) and a mean increase of 14% in CI over LV pacing (2.08 L/min/m2±0.22 SEM to 2.38 L/min/m2±0.27 SEM, p=0.0133). Testing at OPT/BL settings for 30-second intervals was performed in 5 of 7 patients. OPT was beneficial in all patients with a mean increase of 10% in CI compared to BL over three respiratory cycles (2.87 L/min/m2±0.33 SEM to 2.60 L/min/m2±0.37 SEM, p=0.009). When comparing the average of three corresponding end-expiratory beats from the three respiratory cycles, OPT was beneficial by 17% over BL (2.76 L/min/m2±0.33 SEM to 2.36 L/min/m2±0.36 SEM, p=0.011). Average MAP and CI measurements when these cycles are combined show that there was significant variation of CI and MAP over the respiratory cycle for both OPT and BL, with cyclic changes about the mean (p=0.0001). Both CI and MAP increased with inspiration. The pattern of variation relating CI to the respiratory cycle appeared different for OPT and BL and approached statistical significance (p=0.0715). Specifically, CI increased and decreased more rapidly for OPT. The pattern of variation relating MAP to the respiratory cycle was not different for OPT and BL (p=0.9787).

These results indicate that BiVP at optimum AVD significantly enhances CO in patients with AVB during open-heart surgery. Although optimum AVD setting was patient specific, in each case BiVP was associated with significant improvement in CO compared with RV or LV pacing. This example systematically studies acute effects of pacing protocol modification at constant heart rate in patients who require pacing for AVB after CPB during open-heart surgery. Physiologically, lead placement may be as or more important to optimizing ventricular function. The relationship between AVD and CO is related to chamber mechanics through optimization of ventricular filling. An excessively long or short interval is known to result in sub-optimal chamber filling, which contributes to mitral regurgitation. AVD testing in this study supported this premise by demonstrating that extreme values (90 ms, 270 ms) were detrimental to CO. The effect of VPS on parameters of acute systolic function has been studied in patients with left bundle branch block. These studies showed that in patients with dilated cardiomyopathy or congestive heart failure, BiV stimulation was significantly more beneficial than RV pacing alone. This study examined the effect of VPS on CO in patients with AVB after CPB during valvular heart surgery. Using direct real-time measurements of CO from an ultrasonic aortic flow probe, this study showed a significant benefit of BiVP over RV or LV pacing alone. This suggests that typical protocols utilized for perioperative pacing in patients with regular atrial rhythm consisting of DDD mode pacing with temporary bipolar right atrial and RV wires should be questioned.

Figure 10A:
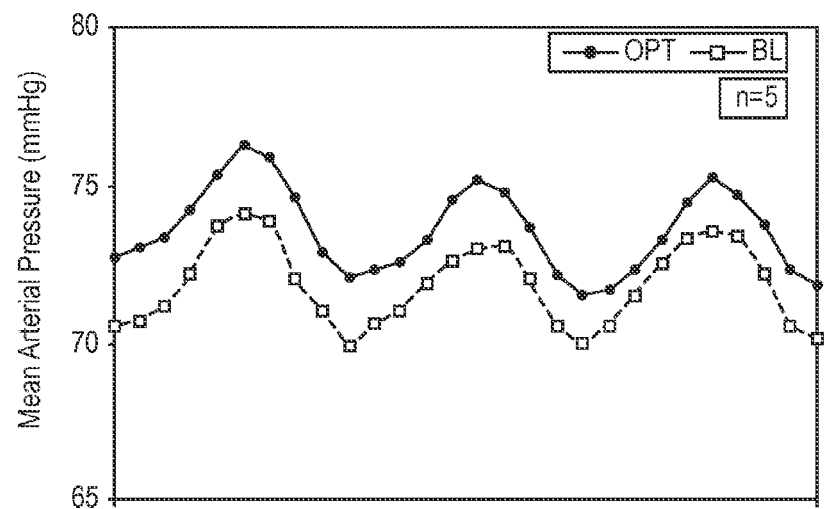
FIGS. 10A and 10B illustrate variation of mean arterial pressure and cardiac index across three respiratory cycles for two pacing settings. Values are averaged from five patients. Mean arterial pressure is shown in FIG. 10A and cardiac index is shown in FIG. 10B. Time is expressed in percentage of the respiratory cycle. Black circle indicates optimum setting; black square indicates baseline setting.
Figure 10B:
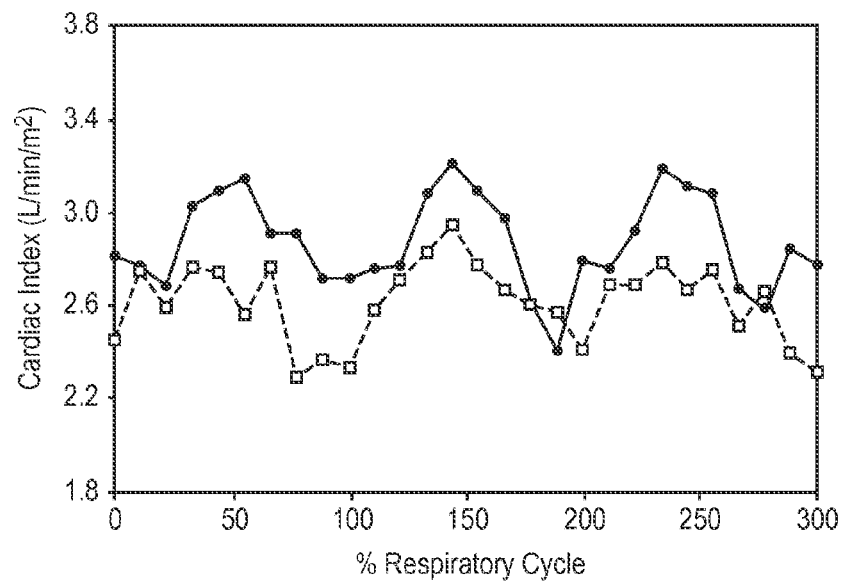
Figures 11A, 11B, 11C:
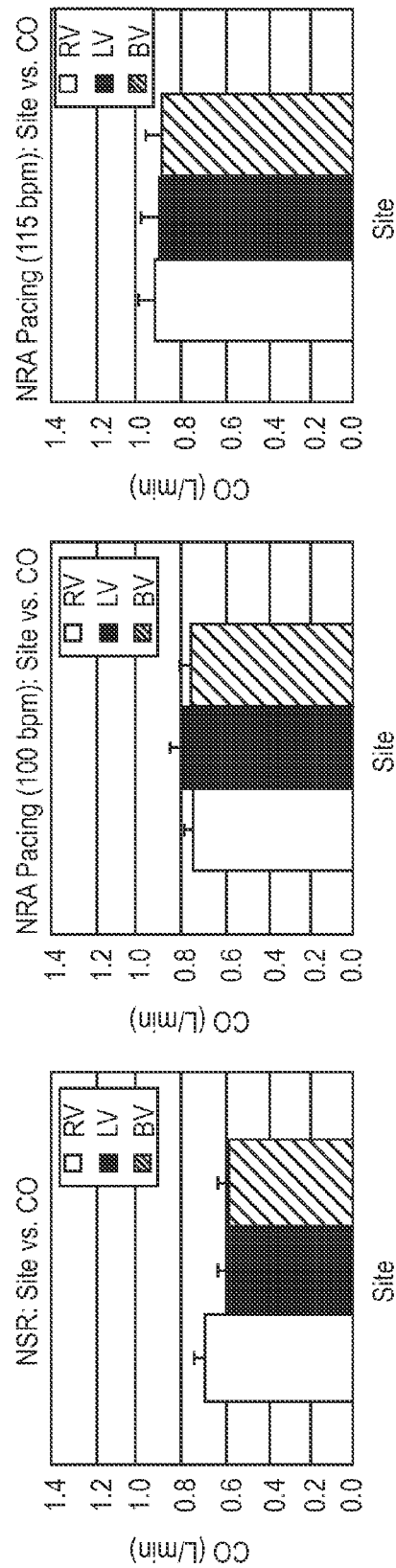
FIGS. 11A-C illustrates the effect of atrial pacing rate and pacing site on cardiac output in pig with ethanol induced third degree heart block.
Figure 12:
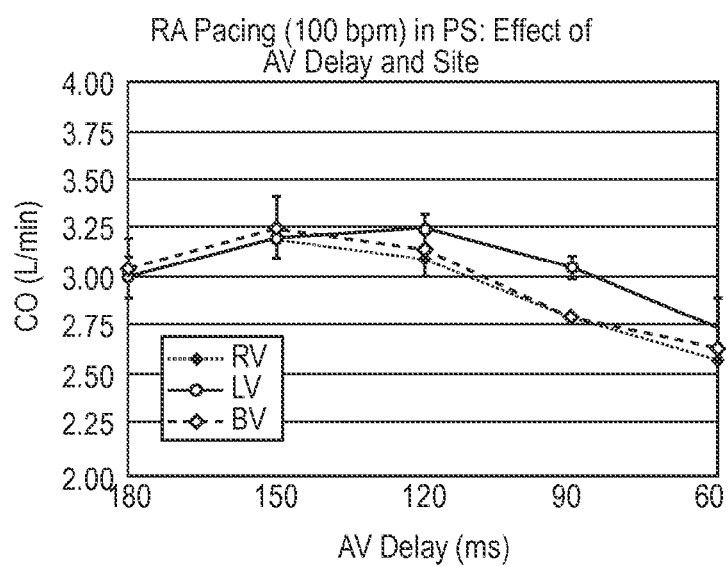
FIG. 12 is a graphical illustration of the relationship between CO, AVD and VPS during acute pulmonary stenosis.
Figure 13:
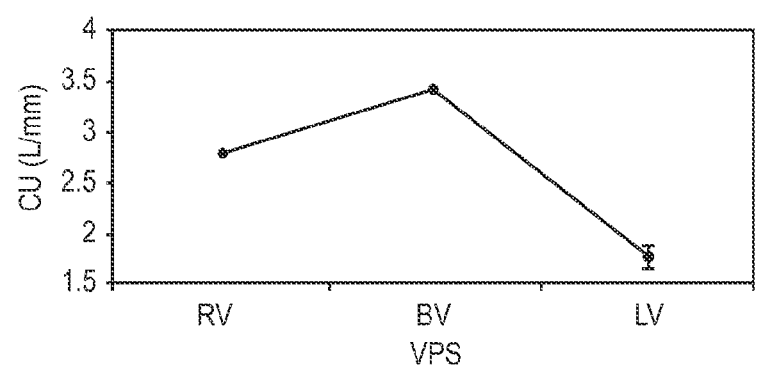
FIG. 13 illustrates the effect of pacing site location on CO after CPB/thombectomy.
Figure 14:
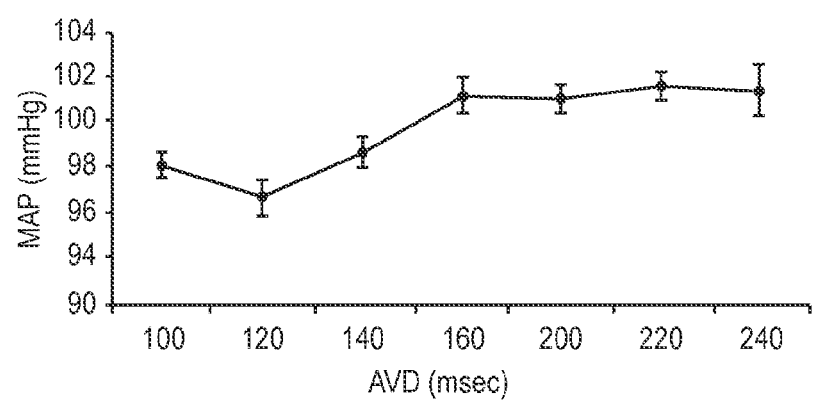
FIG. 14 illustrates the effect of AVD on MAP during BiVP.
Figure 15:
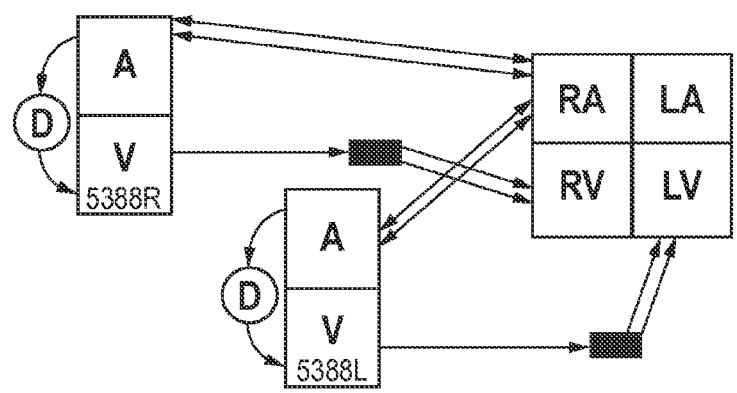
FIG. 15 depicts a schematic of variable RLD BiVP system. The heart is on the right, and the pacemaker is on the left.
Figure 16:
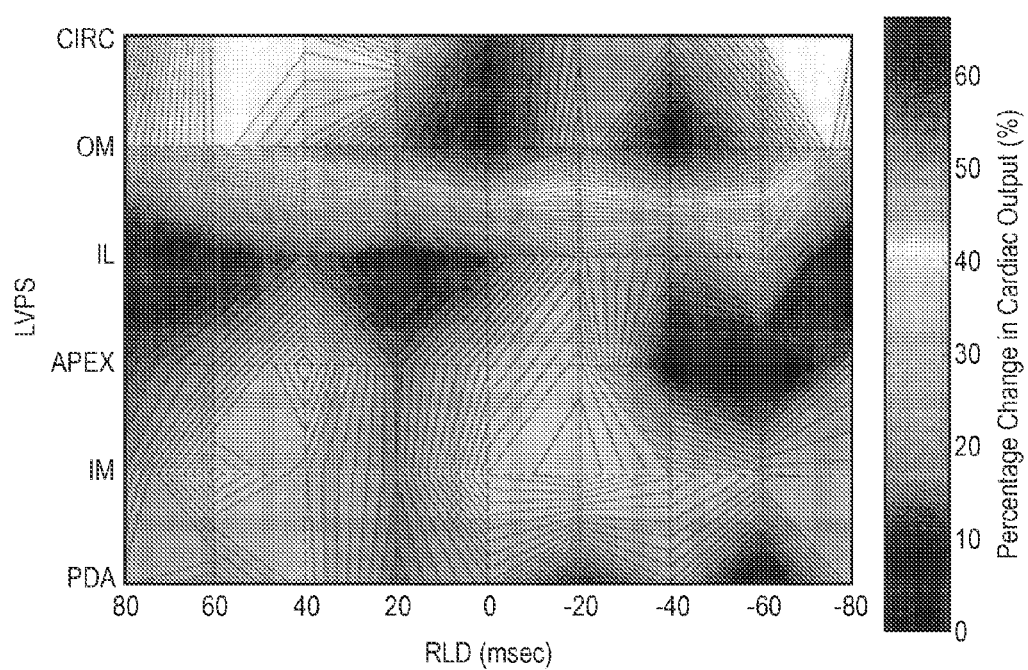
FIG. 16 depicts a response surface with LVPS on the ordinate, RLD on the abscissa and percentage change in CO represented by a red-to-blue color map by linearly interpolating between measured values. Contour lines represent 1% changes in CO.
Figure 17:
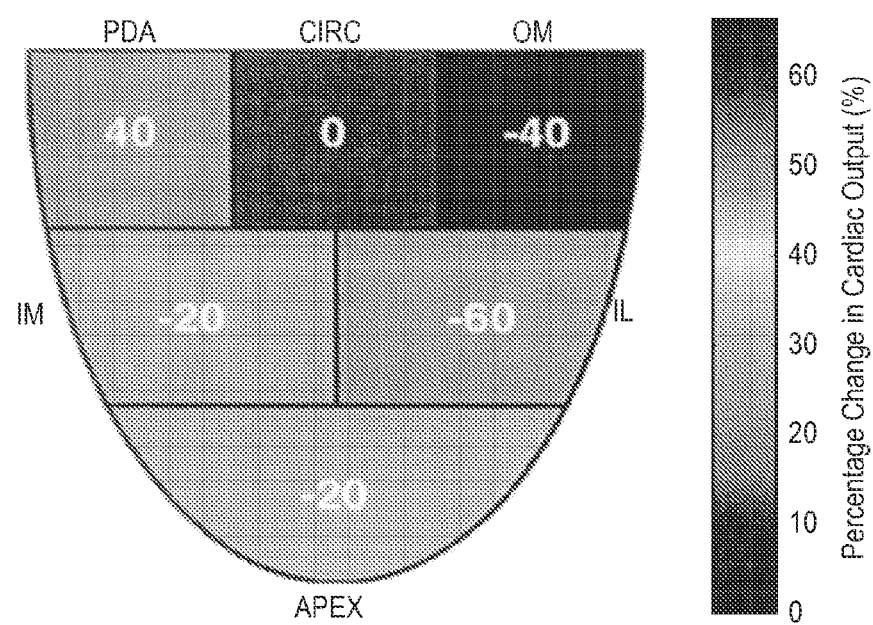
FIG. 17 depicts an LV map showing maximal CO improvement for each LVPS and corresponding RLD (in white).
Figure 18:
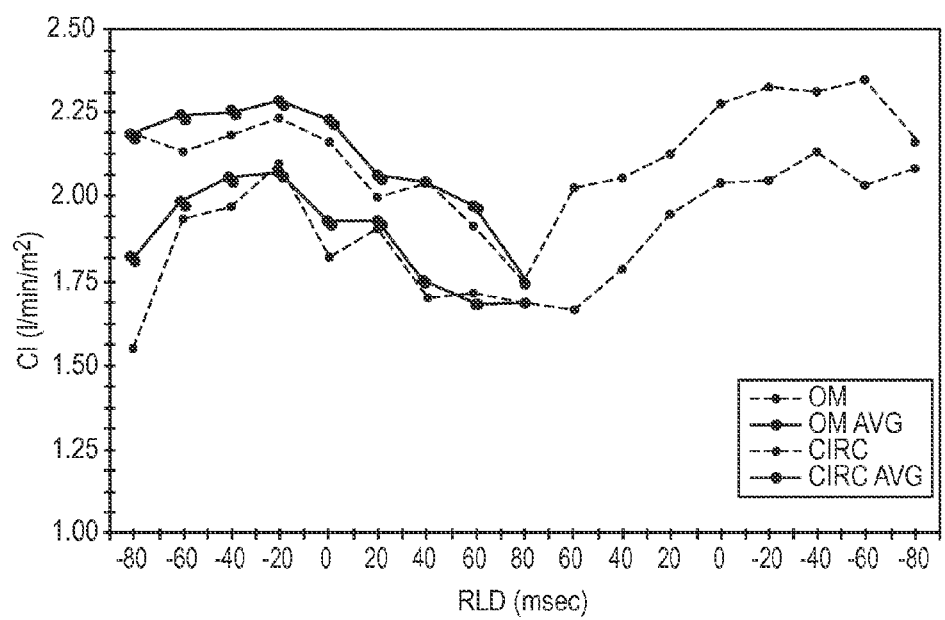
FIG. 18: With HR=90 bpm and AVD=150 msec, DDD BiVP was performed at the OM and CIRC sites as RLD was varied from −80 to +80 and back to −80 msec in 20 msec increments for 10 sec intervals. CI for each setting was averaged over one respiratory cycle.
Figure 19:
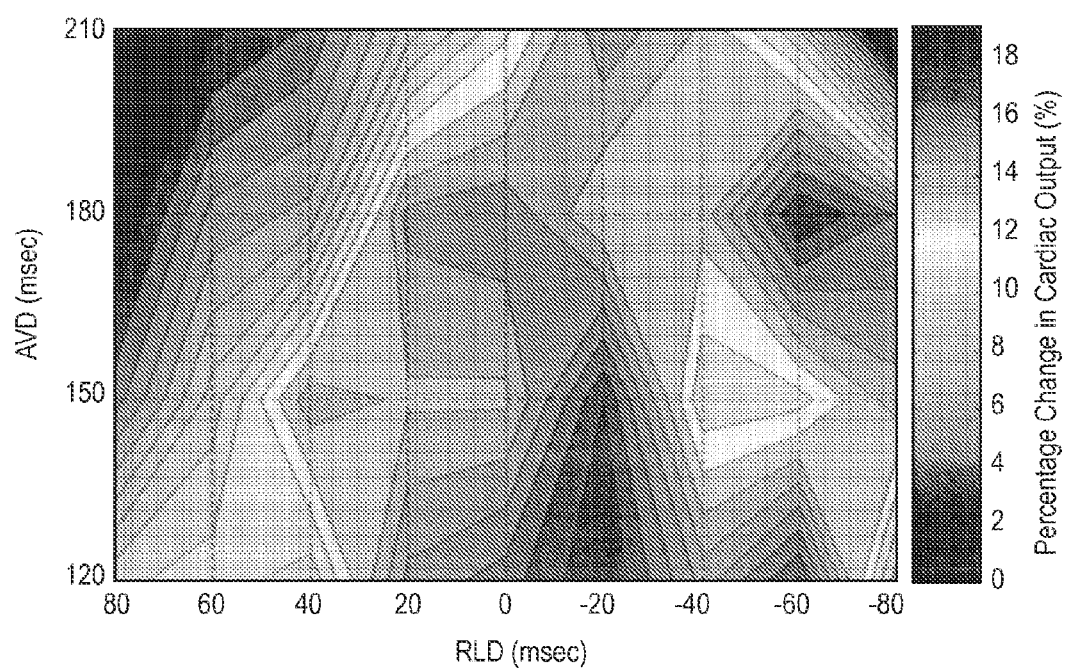
FIG. 19: With HR=110 bpm, DDD BiVP with RLD=0 msec was performed as AVD was varied from 90 to 210 and back to 90 msec in 30 msec increments for 40 sec intervals. At the optimal AVD, RLD was varied from −80 to +80 and back to −80 msec in 20 msec increments for 40 sec intervals. At the optimal RLD, AVD was tested again. CI for each setting was averaged over the last 10 sec of each interval. Finally, the optimal settings were compared to atrial pacing for 60 sec intervals.
Figure 20:
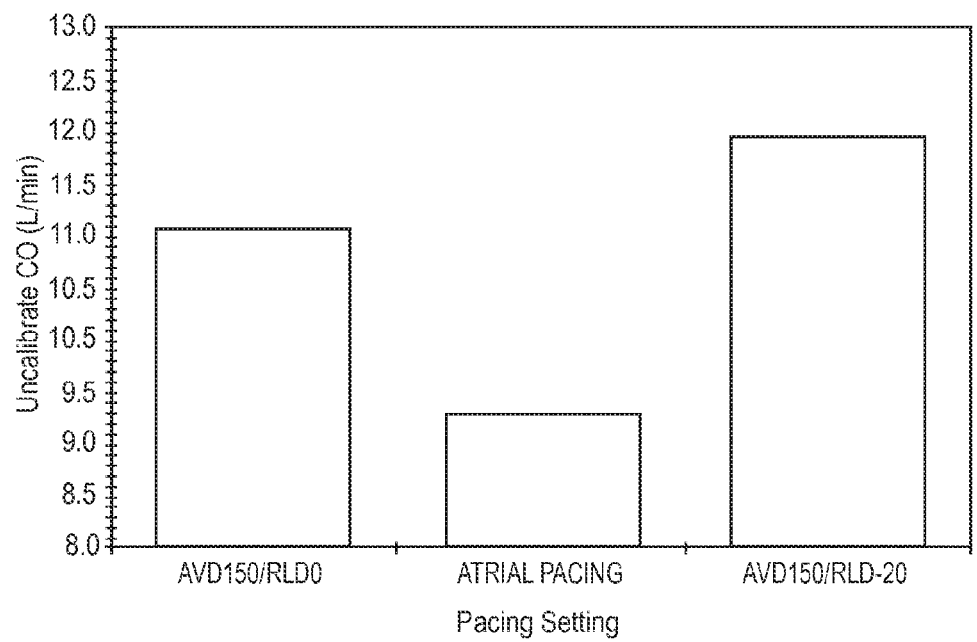
FIG. 20: Response surface with AVD on the ordinate, RLD on the abscissa and percentage change in CO represented by a red-to-blue color map by linearly interpolating between measured values. Contour lines represent 1% changes in CO.
Figure 21:
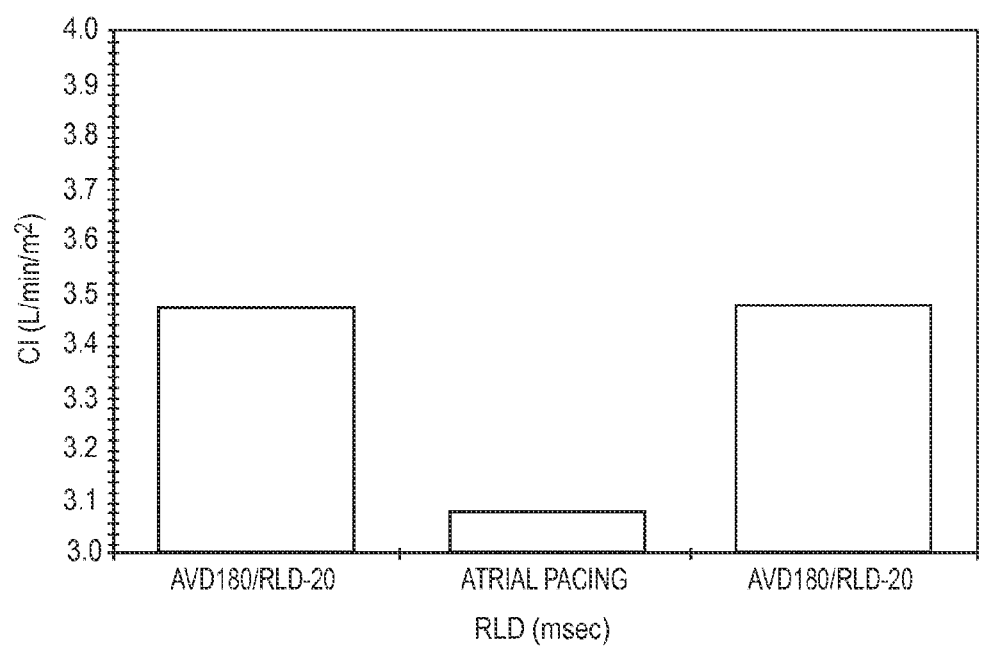
FIG. 21: Comparison of optimal (sequential) BiVP to simultaneous BiVP and atrial pacing alone.

During longer testing intervals, BiVP remained superior to BL with an average improvement of 10% in CI over three respiratory cycles. The improvement was greater (17%) over the average of the corresponding end-expiratory beats in each of the three respiratory cycles. The difference between CI values over three respiratory cycles and the corresponding end-expiratory beats in each cycle is shown in FIGS. 10A-B. In this figure, CI values varied over the respiratory cycle with lowest values at end-expiration and highest values at end-inspiration.

LBBB has been shown to correlate with left ventricular dysfunction. The majority of benefit seen with BiVP is due to the deleterious effects of single-site ventricular pacing. This effect changes the activation sequence, generating regions of early and delayed contraction. Early shortening at the pacing site is wasted work as ejection has not occurred. Late activation of the region remote to the pacing site occurs at higher stress as the paced region has already developed tension. The effects of optimized pacing on interventricular synchrony in experimental models of acute ventricular failure have been investigated using LV and RV pressure signals. During RV pressure overload, pacing at an optimal setting improved interventricular synchrony compared to a suboptimal one. The invention also provides for intraventricular synchrony in these models by echocardiography using M-mode and tissue Doppler imaging. Such analyses would be appropriate for clinical studies.

Historically, definition of mechanisms and treatment of arrhythmias have been accelerated in the operating room by direct exposure of the epicardium to mapping and interventions. This advantage might resolve issues in endocardial BiVP like whether localization of wall motion abnormalities or conduction delays defines an optimum site for LV electrode placement and whether lead localization is critical. There may be patients with isolated RV dysfunction in whom there is no role for BiVP. Correlations between preoperative QRS duration and hemodynamic benefit and between QRS shortening and improved ventricular function have also been described.

With respect to technical aspects of the study, we are concerned about application and removal of the ultrasonic flow probes. The housing of these probes is rigid and requires manual compression of the ascending aorta during both application and removal. For this reason, we have decided to use scissor-type electromagnetic probes to avoid this manipulation. Previous studies suggest that absolute flow measurement is somewhat less accurate with electromagnetic probes, but sensitivity to small changes in flow appears sufficient. Calibration against thermodilution measurements will be done when feasible.

Example 2

Optimized Perioperative Biventricular Pacing

Experimental data suggest that BiVP increases SV with no increase in myocardial oxygen consumption (MVO2). Stroke volume (SV) was measured by echo-Doppler in a substudy of the InSync III trial. Optimization of right-left delay (RLD), the delay between electrical stimulation of the right ventricle (RV) and LV in BiVP, increased SV 12% vs. no pacing (NoP), while standard BiVP with RLD=0 increased SV 5% vs. NoP. Experimental data suggest that BiVP increases SV with no increase in myocardial oxygen consumption (MVO2). Animal studies in our laboratory support the critical importance of RLD timing.

Optimized BiVP thus might be a valuable adjunct to the treatment of LVD or RV dysfunction (RVD) after cardiac surgery (open heart surgery, OHS) for acquired (AHD) or congenital (CHD) heart disease. Very little is known about BiVP in this setting. OHS frequently evokes ACHF, with perioperative requirements for beta agonists, phosphodiesterase inhibitors, afterload reducing agents, diuretics, balloon pumps (IABP) or LV assist devices (LVADs). CFN can be depressed 24-48 hours to many days postoperatively. ACHF is caused by global or regional ischemic injury, inflammation, myocardial edema, and other factors. Surgical results may also be imperfect, including residual mitral regurgitation (MR) after coronary artery bypass (CABG) and/or valve repair, periprosthetic leaks producing aortic insufficiency (AI) or MR, as well as pulmonary stenosis (PS) and/or insufficiency after repair of tetralogy of Fallot (ToF). Afterload mismatch reduces EF after correction of chronic MR or tricuspid insufficiency (TI) and in some cases after LV aneurysmectomy (LVAnX). Pulmonary hypertension occurs after cardiac allografting. Understanding effects and optimization of BiVP in specific forms of RV or LV pressure or volume overload with and without support by inotropes and afterload reducing agents (DRIPS) is essential to define guidelines for perioperative BiVP.

This example sets out a randomized postoperative study of temporary BiVP beginning (TBiVP) at the conclusion of cardiopulmonary bypass (CPB) vs. NoP in patients with preoperative LVD and IVCD. The following parameters will be optimized: RLD, heart rate (HR), atrioventricular delay (AVD), and ventricular pacing site (VPS) in random sequence. The optimum (OPT) protocol is called POPT. Preliminary data have demonstrated feasibility and that TBiVP after CAB can increase cardiac output (CO) by as much as 30%. The invention provides that TBiVP will increase CO and cardiac index (CI) more than 15% compared to NoP as measured by thermal dilution (TD) methods 12-24 hours postoperatively. The example provides for defining POPT at three points within 24 hours of surgery. The example also provides for an examination of which forms of cardiac dysfunction (CDF) benefit from TBiVP and effects of TBiVP on direct and indirect measures of perfusion and CFN. This example provides for the analysis of survival, length of intensive care unit (ICU) stay, incidence of arrhythmias, and the cost of postoperative care.

Pacing Methods.

Pacing algorithms are commonly described by a three letter code identifying the chamber paced (A=atrium, V=ventricle, D=both), the chamber sensed (A, V, D, or O=none), and the algorithm used (I=inhibited, T=triggered, D=both, O=None). FDA approved pacing systems include demand systems for single chamber VVI or atrial (AAI) pacing. DDD systems maintain physiologic synchrony of atria and ventricles. Both endocardial (transvenous) and epicardial leads are approved for use with these pulse generators. A typical DDD system employs a single atrial lead and a single ventricular lead. These leads are unipolar or bipolar (one or two conductors). Unipolar systems use the patient's body as the indifferent electrode. Transvenous leads for DDD pacing are usually placed in the RA and RV. Epicardial leads are placed on the outer surface of the RA, RV, left atrium (LA) or LV. Functions of these leads include sensing intrinsic electrical activity and pacing at low energy. Pacing systems analyzers and temporary external pacemakers are connected with removable epicardial wires for temporary pacing after OHS. Parameters are adjusted with calibrated dials. Implantable pacemakers are adjustable using programmers that communicate by telemetry.

BiVP can improve CFN while reducing MVO2. BiVP is more effective in patients with very low EF and long IVCD of LBBB configuration and is more effective when the LV lead is placed at the most delayed site of LV contraction. Endocardial BiVP may be effective in atrial fibrillation (AF) as well as NSR, and BiVP can reduce the severity of MR. As with AVD, the effect of RLD is not predictable in any given patient and varies over time.

Perioperative Monitoring:

The adult OHS patients typically have a radial artery line providing systolic pressure, diastolic pressure, and mean arterial pressure (MAP). An electrocardiogram (ECG) provides HR through R wave detection. A fingertip oximeter provides arterial oxygen saturation. A Swan-Ganz (SG) pulmonary artery (PA) catheter provides RA, RV, and PA pressure. The SG catheter also provides PA wedge pressure; CO is measured with ID methods. Some SG catheters provide mixed venous oxygen saturation (O2sat) through oximetry. While both O2sat and TD methods can be used to measure CO, these parameters are cumbersome for TBiVP optimization.

Flow Measurement:

Median sternotomy provides access to the ascending aorta (AAo) and PA, allowing measurement of SV by ultrasound transit time flow probes (UFP) or electromagnetic flow probes (EMF). UFPs are found to be reproducible and accurate for laminar flow, because of accurate measurement of the baseline for zero flow. Properly positioned, UFPs provide instantaneous flow velocity, and a digital readout of CO, with CO=SV×HR. PulseCO provides beat to beat measurement of SV with graphical output vs. time. The comparisons with UFP indicate that PulseCO can accurately measure relative changes in SV, even without lithium calibration. However, changes in HR as well as vasoactive agents can introduce small errors into PulseCO data. While less accurate for absolute flow, EMF probes are less potentially traumatic than current UFPs and are equally sensitive, accurate and expeditious for measuring changes in CO and SV.

Heart Rate:

The determinants of LV SV are preload or end-diastolic volume (LVEDV), afterload (reflecting SVR and ventricular dimensions), and contractile state. Under physiologic conditions, there is considerable cardiac reserve. During exercise, increased venous return augments preload, with secondary increases in CO and SV. CO can increase without an increase in HR by a Starling effect of increased venous return. The effect of HR on CO is dependent on the determinants of SV. Increased HR tends to decrease SV by reducing diastolic filling time and preload. The net effect on CO is determined by the relation CO=SV×HR, but venous return must increase in order for CO to increase. The importance of HR after OHS may be altered by decreased cardiac reserve. Treatment of postoperative low CO includes optimization of preload (with volume administration), afterload (with vasodilators), and contractility with inotrope administration). In critically ill patients, SV may be essentially fixed, with little benefit from further increases in preload, afterload, or contractility. Under these circumstances, increased FIR is required to increase CO. Increasing HR increases MVO2 and can cause myocardial ischemia and arrhythmias.

After OHS, paced HR may affect systolic or MAP. Mathematically, CO=MAP/SVR. An increase in MAP indicates an increase in CO if SVR is not altered by reflex changes or other factors. MAP and systolic pressure are not linearly related, because systolic pressure is dependent on both MAP and pulse pressure. Pulse pressure is affected by SV, SVR, and arterial compliance. The invention provides methods of using changes in MAP and/or systolic pressure to estimate changes in CI.

Atrioventricular Delay:

Dual chamber pacing protocols optimize ventricular filling by synchronizing the initiation of ventricular systole with the end of the atrial contraction. For patients with regular atrial rhythm, AVD begins with RA depolarization or stimulation and ends with RV depolarization or stimulation. The AVD in a permanent pacemaker is typically about 150 msec during atrial sensing and about 200 msec during atrial pacing. The differential of about 50 msec allows for IAD, the interval between the atrial pacing stimulus and the P wave. IADs are prolonged to from about 150 msec to about 200 msec in some patients. A 200 msec IAD combined with a 200 msec AVD will produce simultaneous RA and RV contraction, eliminating the atrial kick. Variable IAD and conduction time from RA to LA or atrioventricular (AV) node to RV and LV explain why OPT AVD can improve CO in some patients.

The invention provides methods of optimizing the lead location and other parameters of BiVP so as to improve SV after OHS by more than 10% without increasing MVO2 or arrhythmias. The InSync III, approved by the FDA in 2003, is an implantable pacemaker with programmable RLD. For clinical studies, DDD/BiVP (RLD=0) were obtained by connecting the ventricular output to both the RV and LV. For laboratory studies of variable RLD, two 5388 Medtronic Dual Chamber units were employed. One was connected to epicardial RA and RV electrodes. The second was connected to the RA and LV. The AVD on each unit determined the RLD. To pace the RV first with an AVD of 100 msec, the AVD on the RV pacemaker was set at 100 msec. If the desired RLD was 60 msec, the AVD on the LV pacemaker was set at 160 msec. Blanking or reduced sensitivity prevented inhibition by RVPc. Tables guided manual settings for AVDs from about 60 to about 210 msec with RLDs from +80 (RV first) to −80 (LV first). In one embodiment, one can use a computer controlled automatic system to deliver any desired range of AVDs and RLDs.

Pig Experiments:

Experiments are performed in adult domestic pigs under general inhalation anesthesia. Following median sternotomy, temporary bipolar epicardial pacing electrodes are placed on the anterolateral RA, anterior RV, and posterior LV. Animals are heparinized and instrumented for ECG, RV/LV/Arterial pressure, and CO by UFP. Data are digitized and stored in MacLab. 2-DE is videotaped. Sonomicrometry and pressure-COND are employed selectively.

The BiVP system is tested to confirm RA, RV, and LV sensing and pacing. Third degree heart block (HB) is induced with sequential 0.05 ml injections of absolute ethanol into the area of the His bundle. DDD pacing is initiated, and hemodynamic stability is confirmed. HR, AVD, VPS, and RLD are varied per protocol, while control hemodynamics and 2-DE are recorded in duplicate. Pathologic loading is induced, and data recording is repeated. CO-AVD and CO-RLD relations are analyzed. The RLD-CO relation at the best AVD is analyzed for statistical significance of trends relating CO to RLD. Wall motion, ventricular geometry, pressure-conductance loops, sonomicrometry, and other parameters are compared at the best and worst RLD in the RLD-CO plot (at the best AVID).

RV pressure overload was tested in critical PS (CO half of control) and severe (RV systolic pressure twice control) PS. TI (RV-RA connection) and MR (LV-LA connection) was simulated using a ventricular-atrial conduit. A UFP on the conduit and a snare allowed retrograde flow to be monitored and regulated.

Induction of Critical PS:

A pulmonary snare is tightened to decrease CO 50%. A pulmonary snare is tightened to decrease CO 50%. Increased RV pressures distort the LV, with flattening of the IVS. CO is plotted against the offset from OPT RLD at two different heart rates. Peaked relations are revealed, and a 20 msec offset in RLD from OPT reduces CO 15-20%. Similar data have been derived in models of MR, TI, and alternating PS and TI in the same animal. In contrast to PS, where POPT requires a positive RLD (RV first), TI requires a negative RLD (LV first) for optimum hemodynamics.

In severe PS we identified changes in septal flattening related to timing of the pacing protocol and were able to demonstrate statistically significant improvement in LV eccentricity associated with POPT. These experiments support the view that BiVP is effective in acute heart failure, that POPT is load dependent and possibly load specific.

Ultrasonic flow probes have been used to optimize biventricular pacing immediately after cardiopulmonary bypass, improving cardiac output (CO) by 10%; however, flow probes must be removed with chest closure. The PulseCO system (LiDCO Limited, Cambridge, UK) may extend optimization into the postoperative period, but controlled validations have not been reported. Six anesthetized pigs were instrumented for right heart bypass. Flow was varied from 3 to 1 L/min and then back to 3 in 0.5 L/min increments for 60 second intervals. CO was measured by ultrasonic flow probe on the aorta and by PulseCO using a femoral arterial line. PulseCO and flow probe accurately measured CO (PulseCO R2: 0.79-0.95; flow probe R2: 0.96-0.99). At flow of 2 L/min, when the heart was paced 30 bpm over the sinus rate, PulseCO falsely indicated an increase in CO (2.13 vs. 2.30 L/min, p=0.014). When mean arterial pressure was increased by 20% using a phenylephrine infusion, PulseCO falsely indicated an increase in CO (2.13 vs. 2.47 L/min, p=0.014). When mean arterial pressure was decreased by 20% using a nitroprusside infusion, PulseCO falsely indicated a decrease in CO (2.13 vs. 1.79 L/min, p=0.003). The correlation coefficient for PulseCO and flow in six laboratory studies was 0.87-0.98. PulseCO is attractive because real time data display allows beat-to beat assessment of changes in hemodynamics. SV derived from the arterial pulse contour is multiplied by HR to obtain CO. Calibration in L/min requires lithium injection, but this is unnecessary for TBiVP optimization, where relative changes in CO are the primary concern. PulseCO is practical in the closed chest where UFP is not, allowing extension of clinical studies to patients in the ICU.

Clinical Studies:

Patients with 2° or 3° heart block (HB) were studied at the conclusion of CPB. BL pacemaker settings were defined by the surgeon, and HR was not further modified under the protocol. Using a sterile UFP on the ascending aorta, the research team adjusted AVD to optimize CO. At the OPT AVD, VPS was optimized, testing LV, RV, and BiVP. Each combination was tested for 10 seconds. OPT-BL-OPT settings were then alternated for 30 seconds each, and data were averaged over three respiratory cycles (RCs). Testing was completed within 5 minutes. Alteration of inotropes, vasoactive drips and/or volume infusion were not required during the protocol. The protocol was completed in 7/7 patients who developed HB. The primary lesions were severe AS (3), severe AI (2), and severe MR (2). Patient data are presented below.

| Study No. | Operation | Diagnosis | HB | Atrial Rhythm | Preop EF | ORS (msec) |
|---|---|---|---|---|---|---|
| 2 | AVR | AI, SBE | 3° | NSR | 40% | 140 |
| 4 | AVR, CAB Gx4 | AS, CAD | 3° | NSR | 40% | 106 |
| 5 | AVR | AI | 3° | NSR | 45% | 148 |
| 8 | MVR, CAB Gx1 | MR, CAD | 3° | NSR | 23% | 164 |
| 9 | MVR, TI repair | MR, TI | 3° | NSR | 35% | 146 |
| 12 | AVR | AS/AI | 1° | NSR | 55% | 164 |
| 14 | AVR, MVR | AS/MR | 3° | NSR | 45% | 100 |

AVR, MVR = aortic, mitral valve replacement. SBE = bacterial endocarditis. CAD = Coronary Disease Results:

Real-time UFP SV proved valuable for POPT. To avoid confounding effects of partial cycles, 30 second data was averaged over three full RCs. Some of this data was not useful because of effects of premature beats. In 5 patients, 3 RC data indicate a 9% CI benefit of TBiVP. Data were available from a larger number of patients when two beats at end-expiration (EE) were used. Thus, the average benefit in 7 patients in two beats at EE was 22%. Differences in EE and 3 RC data are due to variable effects of BiVP during the RC. The improvement in CI with POPT vs. BL was due to VPS (BiVP vs. RV or LV). HR was not altered, and an AVD of 150 msec was appropriate in all of the patients studied. The AVD-CO relation in the HB study is similar to what we find experimentally in pigs with FIB.

The AVD-CO Relation in a Patient Following CPB/MV Repair:

BiVP capability was added to a previously implanted ICD/DDD pacemaker by adding an epicardial LV lead. AVD was varied by programming the ICD. CO was measured by UFP. After testing, the AVD was permanently programmed to 200 msec, resulting in a CO 30% higher than that from the 100 msec AVD recommended by the manufacturer's representative.

Data were obtained immediately after CPB in a non-study patient with 2° FIB, ventricular tachycardia, ischemic cardiomyopathy (LVEF=25%) and recurring pulmonary embolism from a massive, friable thrombus on an endocardial RV lead. The OHS procedure was embolectomy, endocardial lead removal, and conversion to an epicardial ICD/BiVP system. The VPS-CO relation measured by UFP demonstrated benefits of BiVP vs. RVPc and LVPc. Two weeks later, the patient underwent testing of the defibrillation threshold of his ICD. His chest was not open, and PulseCO was not available. AVD was optimized using the AVD/MAP relation. The data supported an AVD of 220 msec, which was permanently programmed.

Pacemaker:

The InSync III has all the capabilities needed for TBiVP, including programmable RLD. A robust housing for the InSync III was designed which simplifies its use and allows easy cleaning and disinfection. The unit (TInsync) contains a shock mounted InSync III connected by clinical grade wires and connectors to terminals marked for atrial (A), RV, and LV cables. The unit is brought to the OR with connecting cables attached and labelled. Temporary wires from the heart connect to intermediate sterile cables, then to our labelled cables.

Outputs, sensitivities, AVD, and RLD are programmed using an InSync (Medtronic) programmer. Labelled printouts help confirm function of individual lead systems (FIG. 31).

RLD data obtained with the TInsync is illustrated in FIG. 32. UFP data were obtained immediately after CPB for correction of TI and a Maze operation to reverse AF. The patient previously had AV node ablation and a DDD pacemaker for paroxysmal AF. BiVP was tested in the OR for clinical benefit and possible permanent implementation. With pulmonary hypertension and increased afterload after TI correction, her physiology was expected to resemble laboratory studies of PS. This was confirmed. Her RLD-CO relation indicated RV first pacing was optimal, similar to PS lab data. With no clear benefit of BiVP vs. DDD pacing, her pacing system was left intact. The data is the average of two successive runs increasing and decreasing RLD as in the table below. Representative RLD effects in other patients immediately after CPB show both are averages of successive runs alternately increasing and decreasing RLD in linear fashion.

Clinical Studies of TBiVP in LVD:

Preliminary data were obtained immediately after CPB in four patients with LVD and preoperative LVEF<35%. CI measured by UFP was averaged over 3RCs. Results demonstrate an increase of 9% in CI when OPT TBiVP is compared to RVPc. When OPT TBiVP was compared to NoP in two patients with available data, average CI was found to increase 18%. The largest increase in CI for TBiVP vs. NoP observed to date in any patient has been 30%.

Pacing optimization will be assessed in all patients at three time points (Phases 1-3) using different measures of CO. Utility of MAP, EMF, PulseCO, and TD for achieving POPT will be compared.

This invention provides methods to investigate whether optimized TBiVP increases CI vs. NoP after OHS in patients with preoperative LVD and IVCD. The primary endpoint of CI will be measured using EMF, PulseCO and TD, which are objective measurements of CO and CI. Progression across the matrix of determinants of POPT will be randomized to minimize any effect of interdependence of variables on function. The primary endpoint is CI measured by TD in the ICU. The null hypothesis is that there will be no difference in the CI between the two treatment arms (TBiVP vs. NoP). The alternative hypothesis is that POPT will increase CI by 15%. Patients will be randomized after Phase 1 testing. Secondary end points will include urine output, inotrope requirements, incidence of arrhythmias, survival, ICU length of stay, and cost. The importance of AVD and RLD in pressure and volume overload will also be examined within the overall group. TEE data when available will define LVEDA, ESA, EF, eccentricity, and WMAs during 30 second periods at NoP and TBiVP.

Methods for Testing BiVP:

TBiVP will be achieved with a specially housed InSync III pacemaker (TInsync) under programmer control. All studies will be performed in the OR and ICU at three time points. Phase 1 will occur immediately following CPB over 7.5 minutes. Phase 2 will occur during chest closure or in the ICU over 15 minutes. Phase 3 will occur 12-24 hours postoperatively in the ICU over 3 hours. Patients will be randomized to TBiVP and NoP groups immediately after Phase 1.

For eligible patients in NSR as CPB nears conclusion, temporary bipolar wires will be sewn to sites on the RA and anterior RV. Sensing and pacing functions will be tested with the TInsync. An appropriately sized EMF will be placed on the AAo or PA. The PulseCO device will be connected to the arterial pressure monitor. A 12 contact (six pair) flexible electrode array will be placed in the posterior pericardium and connected to the pacing system. The patient will be converted to partial bypass at a flow of 1.0 L/min/M2. Central venous pressure will be maintained at a convenient, consistent level in the range of 5-15 mm Hg by the perfusionist while TBiVP is tested for 10 second Intervals at HR=90, AVD=150, and RLD=−4. Switching between site will be done manually at first, using alligator clips and a clearly marked array of six contact pairs. This will progress eventually to a manual rotary switch and ultimately to computer control. Testing will progress through all six pacing sites twice. The sequence will be provided by form OR1, from a sealed envelope. Multiple OR1s will be prepared in advance, using a random number generator. As data are acquired, the relation between VPS and CI will be plotted in real time. Selection of VPS LV1 and LV2 will be based on this graph. If results are indeterminate, LV1 and LV2 will be determined by previously printed values on form OR1. Bipolar temporary wires will be placed at sites LV1 and LV2 by the surgical team. After the wires are tested, the patient will be weaned from CPB with BiVP active, the parameters above, and VPS from testing and OR1. After the clinical team weans the patient from CPB and adjusts DRIPS and fluid balance, the protocol begins. CO will be measured with and without TBiVP. Testing of long AVDs will be curtailed if programmer electrograms show pacing 20 msec into the QRS. Testing of long RLDs will be curtailed if there is no effect on QRS duration or morphology.

Phase 1:

DRIPS, antiarrhythmics and doses will be noted. Data recording will include arterial pressure, ECG, IAD, flow velocity, CO/SV by EMF and PulseCO, CVP, PA pressures, and 2-DE. Hemodynamics will be digitized and recorded on a digital computer. Data will be recorded as described below, but C-1a and C-1b will be conducted in randomized sequence (RS) per form OR2. Adjustments to volume status, antiarrhythmics, or DRIPS will be made between C-1a and C-1b or between C-1b and C-1c, if required.

AVD:

With BIV configuration LV1/RV, HR=90, VPS=BiV, RLD=0, data will be recorded at AVDs of 90, 120, 150, 180, 210, 240, 270 msec and back to 90 in RS per OR2. Any IAD will require the mandated AVD to be increased proportionately. Data will be recorded for 10 seconds at each AVD, totaling 130 seconds. Optimum (OPT) AVD will be determined by real-time plots of CO against AVD at EE. If maximal CO is equivalent over a range of AVDs, the median value in that range will be used. If results of AVD testing are indeterminate, a nominal value of 150 msec will be used. Total time for this segment is 130 seconds or less if the pacing artifact occurs within the spontaneous QRS complex.

VPS/RLD:

VPS/RLD will be optimized at HR=90 and AVD=OPT. Data will be recorded at VPS=RV, LV1, and LV2. If CO with LV2 is ≥10% higher than LV1, then the BiV configuration will become LV2/RV. Data recording will continue with VPS=BiV at RLDs of (+) 80, 60, 40, 20, 4 msec and (−) 20, 40, 60, 80 msec. Data will be recorded for 10 seconds at each RLD. A second data set will be recorded. Each recording sequence will be randomized, per OR2. POPT will be determined by real-time plots of CO against VPS/RLD at EE. If results are indeterminate, VPS will be BiV at RLD=0. Total time for this segment is ≤230 seconds, less when long RLDs are deferred for pacing within the QRS.

POPT Confirmation:

Testing in VPS/RLD will define an optimum TBiVP protocol identified as POPT(1). Testing over 30 second periods in C-1c will compare POPT(1) vs. NoP vs. POPT(1). Total testing time for Phase 1 is 450 seconds, less if portions are deferred because pacing extends into the QRS complex.

Randomization/End of Phase 1:

The EMF will be removed. Patients will be randomized by envelope to NoP or TBiVP. TBiVP patients will be paced under POPT(1) until Phase 2. NoP will have sham (VVI at 30) pacing. Urine output, inotropes, arrhythmias, and time between phases 1 and 2 will be recorded.

Phase 2:

Hemodynamically stable patients in sinus rhythm from both groups will be retested after approximation of the sternum or after arrival in the ICU. PulseCO will be used to define POPT in Phase 2. Protocols of Phase 1 will be repeated with each testing interval doubled. Whether LV1 or LV2 is used in POPT(1), the other LV site will be used for BiV testing in C1b to define POPT(2). The total time will be 900 seconds, less if portions are deleted for QRS pacing. The conclusion of C-1c, will be followed by 30 second periods under POPT(1), POPT(2), POPT(1) to determine which is superior for continued pacing. If CO decreases more than 10% or MAP decreases more than 10 mmHg at any point in the protocol, testing will be terminated and the previous POPT settings will be restored. NoP patients will continue with backup VVI pacing. TBiVP patients will continue with the updated POPT protocol until Phase 3. Urine output, inotropes, arrhythmias, and time between phases 2 and 3 will be recorded. DRIPS, PA pressure, ECG data and any clinical measurements of CO will also be recorded. TEE recordings will be marked for reference if available.

Phase 3:

This will be conducted 12-24 hours after the patient arrives in the ICU. In hemodynamically stable patients in sinus rhythm, PulseCO will be used to define POPT. Phase 3 will explore a BiVP matrix of HR (intrinsic or 90 bpm), LVPS (LV1, LV2), AVD (5 values, eliminating 90 msec and 270 msec extremes), and RLD (9 values or less). All possible values of this matrix includes 2×2×5×9=180 data points. Single site pacing of LV1, LV2, and RV involves no RLD but adds 30 additional possible data points, totaling 210. There are two additional meaningful points, NoP and atrial pacing only at 90 bpm. The total is 212 points. With 30 seconds for PulseCO equilibration, 106 minutes or one hour and 46 minutes will be required for data collection. For each AVD that is eliminated because of pacing within the QRS interval, 36 BiVP plus six single site data points are eliminated, reducing the data collection period by 21 minutes. For each RLD that is eliminated for pacing inside the QRS complex, 20 data points or 10 minutes of data collection will be eliminated. However, RLDs are likely to be eliminated in pairs at the ends of the spectrum, each pair decreasing the data collection interval by 40 data points and 20 minutes.

Form OR3 will provide a RS list of the 212 HR-VPS-AVD-RLD combinations. Those with extreme values of AVD and RLD will be identified to facilitate manual elimination. Ultimately we will use a digital computer to provide a printed RS of values after entry of the patient's IAD, AVD, and QRS duration.

PulseCO and MAP data will be digitized and sorted by amplitude. At the conclusion of the protocol, the combination resulting in the 10 highest values for CI will be retested. Using a new RS, data will be collected for each of these over 30 seconds, followed by a 30 second washout. Data will be digitized and the combination resulting in the highest CI will be identified as POPT(3).

If CO decreases more than 10% or MAP decreases more than 10 mmHg at any point in the protocol, testing will be terminated and the previous POPT settings will be restored. NoP patients will continue with VVI pacing. TBiVP patients will continue with the updated POPT protocol. Hourly urine output, inotropes, incidence of arrhythmias, and weight gain in Kg. vs. the preoperative day will be recorded. The research team will also record the pacing protocol, DRIPS, ventilator status, pressure, ECG data and any clinical measurements of CO. The unused temporary wires at site LV1 or LV2 will be removed.

End Point Data:

The effect of TIBVP on CO will be determined using TD CO in duplicate in the ICU at the end of Phase 3 during the sequence POPT-NoP-POPT. The duration of these intervals will be determined by the time required to record TD data in duplicate while cardiac rhythm and hemodynamics are stable. MAP, antiarrhythmics, DRIPS, will be recorded during this period. TBiVP will be discontinued when weaning of vasoactive agents is complete.

A final POPT(3)-NoP-POPT(3) comparison will be done using TD CO (if available), MAP, and PulseCO. Pacing will be discontinued and vital signs obtained every ten minutes for 30 minutes to assure hemodynamic stability. The investigators will then disconnect the TInsync and return it to the laboratory for cleaning and disinfection. The surgical team will remove temporary pacing wires. Final data, including inotropes, antiarrhythmics, DRIPS, pressure, ECG data, any clinical measurements of CO, and urine output will be recorded.

Definition and Measurement of Endpoints:

Digitized TEE images will be planimetered to calculate LV end-diastolic area (EDA), end-systolic area (ESA), EF, D1/D2, and WMAs during 30 second periods at BL and POPT. Q2-DE data will be compared by ANOVA. MR, if present, will be compared at NoP and POPT(3) by echo Doppler. Mortality will be defined as patient death within 30 days of surgery.

Significance:

Results will demonstrate whether CI is increased in TBiVP vs. NoP and whether there are related clinical or economic benefits. If clinical and objective benefits are substantiated, TBiVP should be widely applied in appropriate candidates. If POPT is different for phases 1, 2, and 3, then a pacemaker that automatically assesses and implements POPT would become a long-term research goal. Success also would stimulate industry to develop pacemakers for TBiVP with appropriate features.

Cardiac Index:

CI was chosen as the primary end point because it is believed to be the critical post-CPB hemodynamic variable. If CI is not maintained, lactate accumulation and generalized organ dysfunction results in death, even if vasoconstrictors maintain adequate blood pressure. CI by TD in the ICU is the primary end point because it is widely accepted as a gold standard for clinical measurement and is widely available. This will make results of this study directly relevant to current clinical practice. Furthermore, the larger time window and increased stability of the patient in the ICU make that setting more amenable to slower measuring techniques. However, TD is far too cumbersome, slow, and inaccurate to allow it to be used to define POPT.

Phase 1 is characterized by a narrow time window to determine POPT. Accuracy and speed of CO measurement are critical to quickly define POPT and maximize patient benefits. In this setting, the EMF is optimal. Given adequate contact and laminar flow, EMF is fast and accurate in measuring small changes in flow while minimizing potential trauma to the AAo. This technology is ideal for definition of POPT(1). Unfortunately, EMF must be removed for chest closure. PulseCO provides a sorely needed adjunct to Phases 2 and 3. While its speed and accuracy are inferior to the EMF, they appear adequate for definition of POPT when testing intervals exceed 15 seconds. PulseCO is clearly superior in speed to TD for defining POPT.

If major benefits are apparent in the TBiVP group, randomization may become difficult, and crossover from the NoP group can be anticipated. In one embodiment, this was dealt with this by using bipolar pacing systems which result in very small pacemaker artifacts. In another embodiment, the TInsync can be left connected to the NoP patients in VVI mode at a backup rate of 30. The InsyncIII is not capable of an RLD=0; accordingly RLD will be (+) or (−) 4 msec. For patients with intrinsic HR 91-119 bpm, atrial tracking will be used. All patients will have TBiVP in the first 7.5 minutes after CPB.

The invention also provides application of some advanced techniques to define mechanisms of action of BiVP in surgical patients. These techniques include strain and strain rate imaging and area of the normalized LV-RV pressure diagram (see below). We are interested in assessing the effect of changes in inotropic state on POPT requirements in acute cardiac dysfunction.

Micromanometer:

Micromanometers are pre-soaked in sterile saline for 30 minutes prior to calibration. Pressure calibration is done with a column of normal saline in a graduated cylinder. 0 mmHg is recorded as the pressure sensor is placed just below the surface. 10 mmHg is recorded 13.6 cm below the surface.

LV End-Diastolic Pressure (LVEDP) is LV pressure coincident with the R wave of the ECG.

Hemodynamic Data:

Analog data are digitized at 200 Hz (MacLab A/D converter) and stored on a Macintosh G4 Powerbook computer, with data archives on writable CDs. IGOR or MacLAB software allows calculation of standard indices of systolic and diastolic function.

Conductance Calibration:

COND is calibrated by comparing SV by COND and UFP to calculate alpha. Parallel COND is then derived from Q2-DE measurement of RVEDV or LVEDV.

MVO2:

In humans, MVO2 will be measured as the product of the difference in coronary artery O2sat and CS O2sat determined by hemoximeter and coronary flow measured by an intracoronary Doppler catheter placed in the proximal left main coronary artery. This assumes that flow velocity is proportional to volume of flow, which is the case if vessel diameter is constant. Experimentally MVO2 will be measured using the same formula, but a UFP will be placed around the left main coronary artery to determine flow.

Statistical Methods:

For simple designs, with paired data, (i.e. pre and post-op data) a paired t-test will be utilized. For comparison of two independent groups, the standard student's test will be employed; for three or more groups, ANOVA. If we find significance among these groups, a multiple comparison procedure such as the Scheffe test or Tukey's test for pairwise differences will be employed to discern where the differences lie. These methods also control for the potential increase in the Type I error associated with multiple testing. To correct for possible difference in baseline measurements, ANCOVA is the method of choice. This offers adjusted group means, correcting for group differences at baseline. The homogeneity of slope assumption will be tested. If there are repeated measures over time per individual, MMM (Proc MIXED, The SAS System software, SAS Institute, Inc., Cary, N.C.) will be the chosen procedure. This approach estimates the standard errors by modeling the covariance structure of the repeated measures. These measures are inherently correlated within subject. Three of the more common covariance structures include "compound symmetry" for correlations that are constant for any two points in time, "auto-regressive order one" for correlations that are smaller for time points further apart, and "unstructured", which has no mathematical pattern within the covariance matrix. Other covariance structures that will be tested include the Toplitz and the Heterogeneous Compound Symmetry structure. For other independent continuous outcome data, which may be correlated to a number of factors, ordinary least squares linear regression techniques will be utilized. Time-dependent outcome variables may be analyzed using Kaplan-Meier Product-limit estimating techniques.

Two-Dimensional Echocardiography:

2-DE is acquired with a GE/Vingmed CFM 800 or General Electric Vivid 7 Vantage Release (GE Medical, Milwaukee, Wis.), using a hand-held epicardial 5.0 or 7.5 MHz ultrasound transducer and scanning gel (Ultraphonic scanning gel, Pharmaceutical Innovations, Inc. Newark N.J.) to provide a stand-off between the epicardium and the transducer. Using the General Electric Vivid 7 Vantage Release System, LV short axis 2-D images with simultaneous tissue Doppler imaging (in background) are acquired. Imaging frame rate, including tissue Doppler, will exceed 115 fps. The system allows unlimited 30-second capture and storage of digital cineloops. In addition to the 2-DE, time (msec), gain, and offset controlled electrocardiogram is also included in the digitized cineloop. The stored tissue Doppler information will allow strain, SRI, and displacement (Tissue Tracking) to be processed and displayed in qualitative velocity color maps or as quantitative wave forms. For functional comparisons, 2-DE is digitized and videotaped under all conditions of interest. 2-DE data are digitized to calculate LV EDA, ESA, EF, eccentricity, and WMA (see below).

2-DE LV models include Simpson's rule algorithms (stacked ellipsoids) and ellipsoids of revolution. In experimental animals, algorithms have been validated against postmortem PV curves and volume of postmortem casts of LVs fixed at the LVEDP observed in vivo. Current procedure involves 4-chamber) (0°), 2-chamber (62°) and long axis (101°) views traced and reassembled into a Cartesian xyz system. Sixteen stacked disks are constructed with cubic splines and the endocardial surface is reconstructed from multiple interpolated apical and cross-sectional borders.

Q2-DE Calculations. Segmental WMA:

Segmental analysis is used for study of CUD (FIGS. 35,36). Matlab routines now facilitate analysis of global and local LV function. The endocardial borders of digitized end-diastolic and end-systolic short-axis 2-DE LV images are delineated. This is done with manual planimetry by an investigator blinded to the experimental conditions, following American Society of Echocardiography standards. This provides global measures of LV function including EDA, ESA, SA and EFa (FIGS. 37,38). The borders are superimposed (FIG. 39) by alignment of "floating" centroids. Using a modified Fourier analysis technique described by Kass et al., points are interpolated at 100 evenly spaced locations around the border for regional analysis. Radial chords are generated from the centroid to these points, giving radial dimensions of the LV and allowing investigation of regional shape. By measuring the change in length of the chords between time points we get a measure of local wall motion. Regional fractional shortening is calculated by dividing the change in chord length by the initial length (FIG. 40). By tracing the epicardial borders, measures of local wall thickness are obtained (the difference between epicardial and endocardial chord lengths) also permitting calculation of fractional wall thickening. Local fractional shortening and wall thickening provide an index of regional LV systolic function. Local curvature can be measured by differentiating the Fourier series. Combined with pressure data, curvature can be used to estimate local circumferential LV wall stress as described by Janz (169). Measures of regional curvature and wall stress compliment measures of regional shape, fractional shortening and wall thickening, which are reference system dependent, since they describe an intrinsic regional property of the LV that is independent of any external or internal reference system.

LVEDA:

The largest short axis cross section during the cardiac cycle at the midventricular level, generally close in time to the R wave of the ECG. All echo measurements in the steady state are done by averaging results in three separate beats.

LVESA:

The smallest short axis cross section at the level and sectioning plane used for LVEDA. Increased LVESA after CPB can indicate LVD.

EF:

100*(EDA−ESA)/EDA. Increases with EDA or contractility, inversely related to SVR.

LVM:

Calculations are based on three long axis sections (apical long axis, two chamber, and four chamber views). Mass is given by the calculated wall volume (epicardial volume minus endocardial) multiplied by 1.055, the specific gravity of myocardium. In LV short axis cross sections, the epicardium and endocardium define the myocardial ring. Ring area can be converted to LVM based on our previously defined validation equations.

LV Eccentricity:

Ratio of perpendicular minor semiaxes bisecting the IVS (D1) and the papillary muscles (D2). D1/D2 at midventricle calculates eccentricity.

Incidence of Arrhythmias:

The number and duration of any arrhythmias requiring therapy or resulting in an abrupt change of 20 bpm in heart rate or 20 mmHg in systolic arterial pressure will be recorded. This includes sinus bradycardia or arrest, supraventricular tachycardias, ventricular tachycardia or fibrillation, and frequent atrial or ventricular premature depolarizations. The use of antiarrhythmics will also be recorded. The incidence of arrhythmias and the frequency and average dose of antiarrhythmics will be compared in the two groups of patients.

Randomized Sequence of Data Collection:

This defines techniques used in the protocol to progress through an array of determinants of pacing function in random fashion. The intent is to avoid interactions that could cause additive or detrimental effects in successive testing of parameters. This will be accomplished initially by preparing a large number of printed forms as needed for points OR1, OR2, and OR3 in the protocol.

All possible combinations of parameters will be listed and a random number generator used to rank them in an unpredictable order for testing. The forms will be placed in sealed envelopes and selected at random for any given study. The envelopes will be opened when needed in the operating room, and the protocol will be followed. Ultimately, these functions will be assumed by a digital computer equipped with a random number generator and appropriate programs. Calculations will be done in the operating room and printed prior to protocol initiation.

Real Time Data Analysis:

An analog to digital converter will continuously digitize pressure and flow velocity wave forms. Initiation and completion of positive pressure ventilation will be identified from minima in peak arterial pressure or MAP. Flow and pressure will be integrated over complete respiratory cycles or at end-expiration as required by the protocol. The primary measurement, CO, will be calculated and plotted against the intervention active at the time of data recording.

Surface Plots:

This is a two-dimensional surface plot from MatLab (The MathWorks, Inc., Natick Mass.). These routines are readily adaptable to real-time display of digitized data.

LV Pacing Sites:

The prototype array will be expanded to include six sites of interest. These are periapical, mid posterior, mid obtuse marginal, basal posterior, basal posterolateral, and basal obtuse marginal.

Flowmeter Calibration:

An EMF size is selected that gently compresses the aorta. An arrhythmia-free steady state tracing is recorded during duplicate thermal dilution CO measurements. The total area under the flow velocity curve is calculated and set equal to CO to calculate flow/unit area.

Example 3

Figures 22A, 22B:
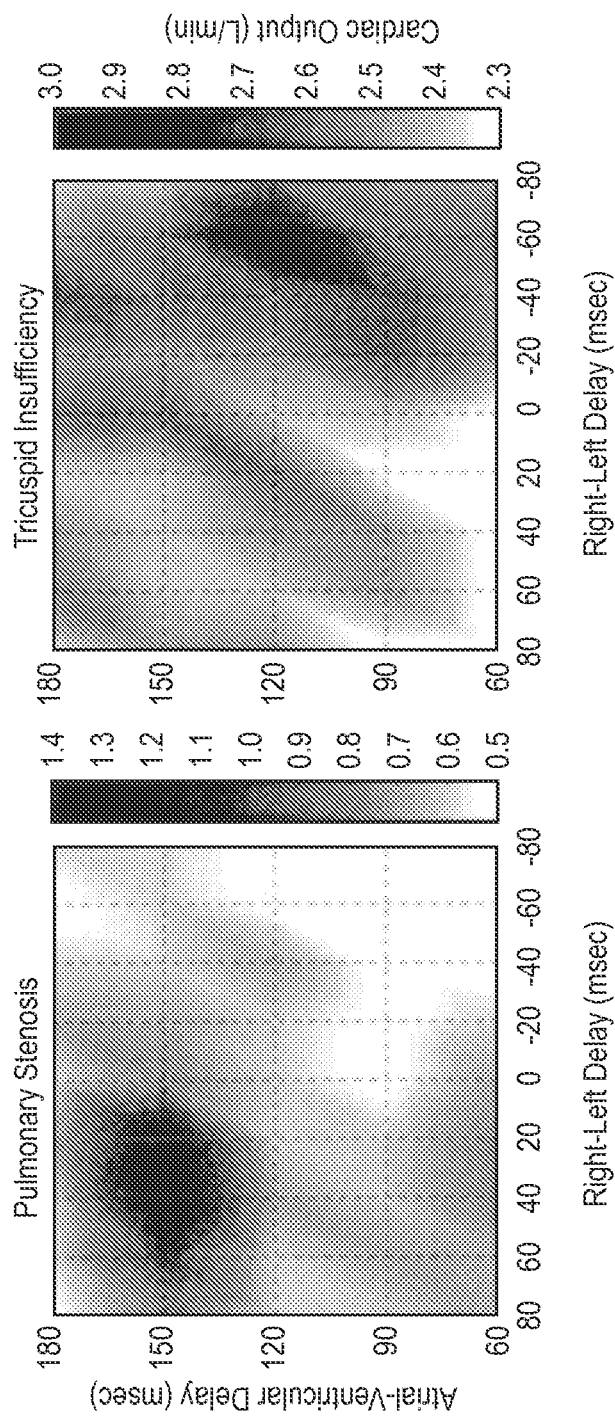
FIGS. 22A and 22B shows representative CO surface plots during BiVP in a pig with pulmonary stenosis (left, FIG. 22A) and tricuspid insufficiency (right, FIG. 22B).

Visualization of the Effect of Atrial-Ventricular and Right-Left Delay on Cardiac Output During Biventricular Pacing Acute optimization of BiVP requires determining the appropriate atrial-ventricular delay (AVD) and right-left delay (RLD) on a patient-to-patient basis. This example examines the utility of CO surface plots for optimization of BiVP. In a study of pulmonary stenosis (PS) and tricuspid insufficiency (TI) in anesthetized pigs with induced heart block (HB), AVD and RLD were varied during BiVP and CO measured using an ultrasonic flow probe. Surface plots displaying CO with variations in AVD and RLD were generated. CO, represented by a red-to-blue color map (the vertical bar), is plotted against varying RLD (80 to −80 msec) on the abscissa and AVD (60 to 180 msec) on the ordinate and linearly interpolated between measured values. FIG. 22 shows representative CO surface plots during BiVP in a pig with pulmonary stenosis (left) and tricuspid insufficiency (right). (Note: Here the color spectrum is displayed as a gray scale map, with black representing the highest CO). The plots show the optimal settings of AVD and RLD, indicated by the darkest area of the surface. CO surface plots allow visualization of the effects of AVD and RLD on CO during BiVP. By use of emerging technologies, CO maps may be useful for determining the optimal AVD and RLD settings for BiVP.

Example 4

Clinical Use of Device in Patient with Dilated Cardiomyopathy

Perhaps for the first time, this illustration of use of the device of the invention has demonstrated the interaction of left ventricular pacing site and timing in a patient with dilated cardiomyopathy. The experiment utilized randomized analysis of site-timing interactions and two-dimensional surface plots.

A 71 year-old male diabetic with recurrent bacteremia and a sizable vegetation on pacemaker-defibrillator electrodes was the subject of this example. Clinical evidence indicated a need to remove the leads on cardiopulmonary bypass. The patient's advanced dilated cardiomyopathy included QRS duration 220 msec, ejection fraction of 15%, moderate mitral regurgitation, and poor coordination of septal and free wall contraction. The clinical plan included extraction of all chronically implanted hardware on cardiopulmonary bypass. Temporary biventricular pacing was indicated until sepsis resolved and a "permanent" biventricular pacemaker-defibrillator could be implanted. An intraoperative protocol including measurement of aortic flow velocity with an electromagnetic aortic flow probe was implemented with informed consent.

Figure 2:
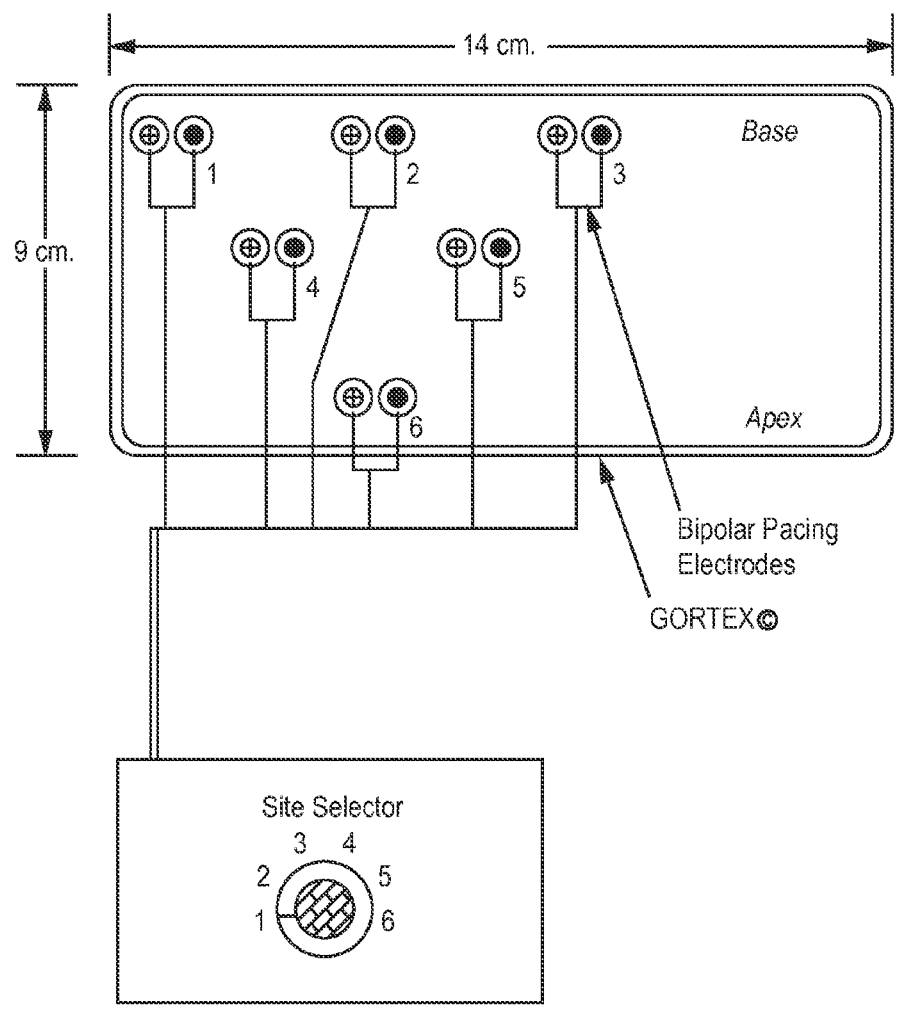
FIG. 2. depicts a custom epicardial pacing array with 6 bipolar-electrodes and a multiplexer.
Figure 3:
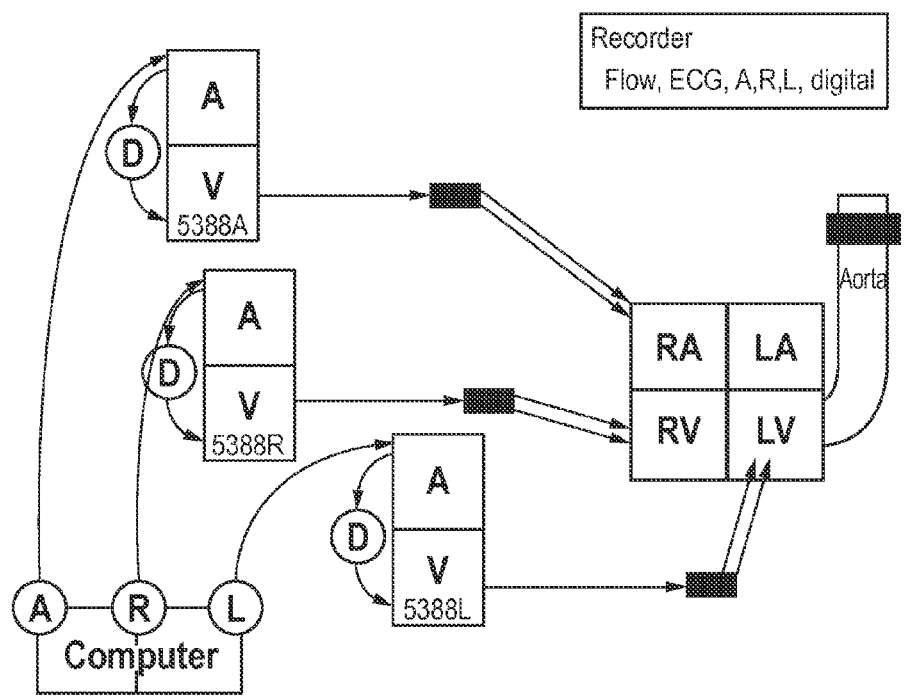
FIG. 3. depicts an embodiment of a computerized pacing system with UFP feedback.
Figure 4:
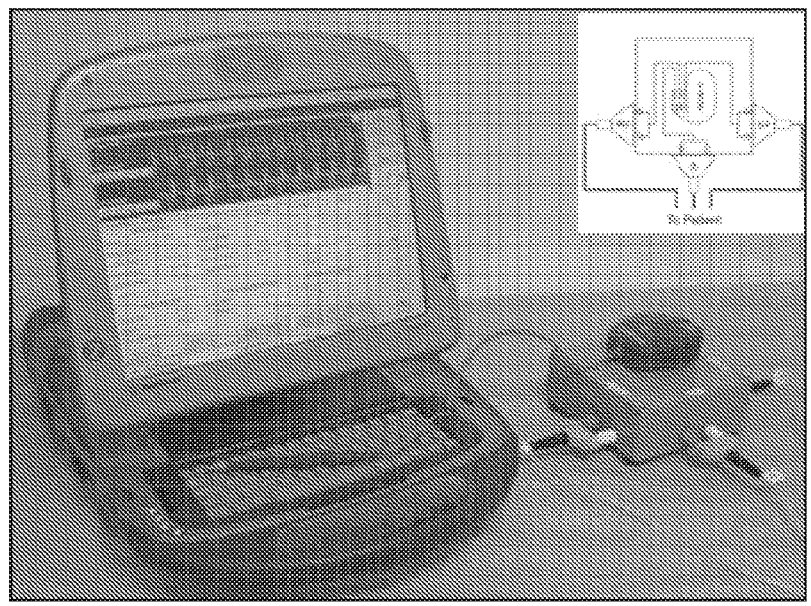
FIG. 4. is a photograph of a system including a computer processor, a display screen and a pacemaker.
Figure 6:
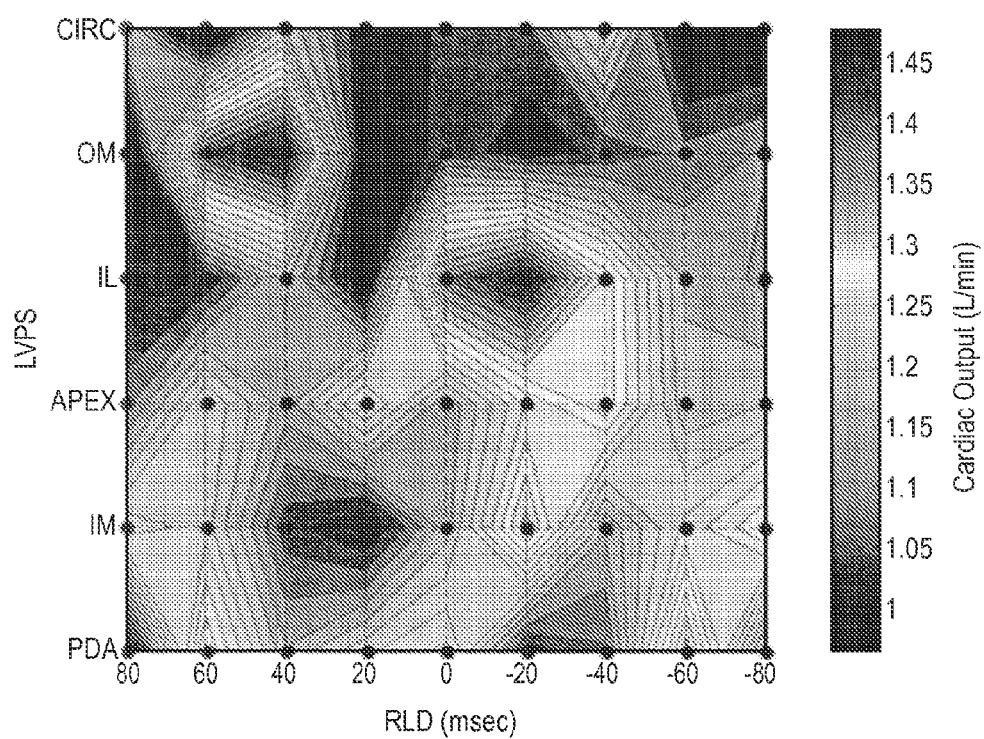
FIG. 6. illustrates a two-dimensional surface map of % change in CO from the surface mean for 54 combinations of RLD and LVPS measured during critical PH/HB and averaged over 5 subjects. Darkest areas of highest % change indicate optimum combinations of LVPS (vertical axis) and RLD (horizontal axis).
Figure 9:
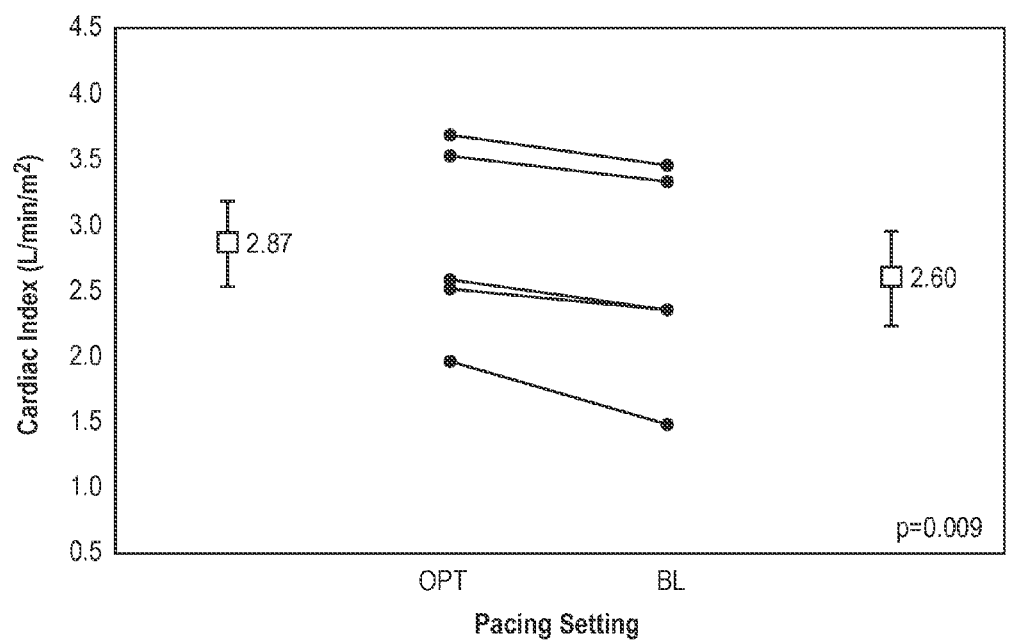
FIG. 9 illustrates a comparison of optimized BiV pacing (OPT) to BL for 30-second intervals which yielded a mean increase of 10% in cardiac index over three respiratory cycles.

While mobilizing the infected leads from the chest wall site and cannulating for cardiopulmonary bypass (CPB), bipolar pacing wires were clipped to the right atrial (RA) appendage and anterior wall of the right ventricle (RV). A 6 bipolar-electrode, epicardial pacing array (FIG. 2) was placed in the posterior pericardium to test left ventricular pacing sites (LVPS). Pacing wires were connected to a temporary pacing unit housing a Medtronic InSync III, including variable RV-LV delay (RLD). An electromagnetic flow probe was placed on the ascending aorta. At a paced heart rate (HR) of 90 bpm and an atrioventricular delay (AVD) of 150 msec, DDD BiVP was tested for 54 combinations of RLD and LVPS implemented in random order over 15 sec intervals. RLD ranged from +80 to −80 msec in 20 msec increments (+RLD=RV first) and LVPS comprised 6 LVPS (apex, infero-medial (IM), infero-lateral (IL), posterior descending (PDA), circumflex (CIRC), and obtuse margin (OM)). Cardiac output (CO) for each RLD-LVPS combination was calculated using customized routines in Matlab, which, after eliminating any arrhythmic beats, integrated the aortic flow tracing over each interval. Initiation of BiVP during this sequence resulted in narrowing of the QRS and an increase in systolic arterial pressure from 104 to 131 mmHg. Changes in pacing settings produced immediate changes in arterial pressure and aortic flow (FIG. 9). CO response was displayed as a response surface for LVPS and RLD (FIG. 64), and maximal CO improvement for each LVPS on an LV map (FIG. 65). Pacing at the OM or CIRC site produced the best CO, with up to 66% improvement with optimal settings:

After lead extraction on CPB, paired permanent unipolar screw-in leads were attached to the CIRC site and capped. Temporary wires were sewn to the CIRC and OM sites, the RA and the RV. RLD had a pronounced effect on cardiac index (CI) for both sites, with an optimal setting of −20 msec producing up to 23% improvement and the OM site 11% greater than CIRC (FIG. 4). Twenty-four hours later, further testing included measurements of CI with the PulseCO™ device, calibrated by thermal dilution. Testing was done from the OM site only. Varying RLD provided up 6% improvement and optimal BiVP a 13% increase over atrial pacing alone (FIG. 6).

Figure 7:
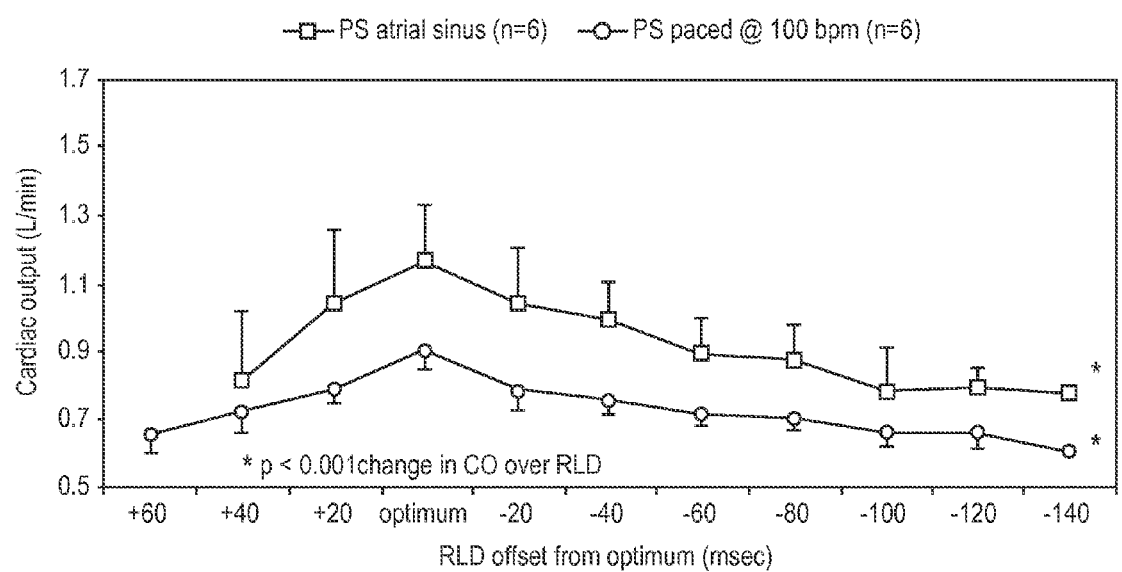
FIG. 7. is a graph of RLD offset from optimum vs. CO in critical PS in pigs.
Figure 8:
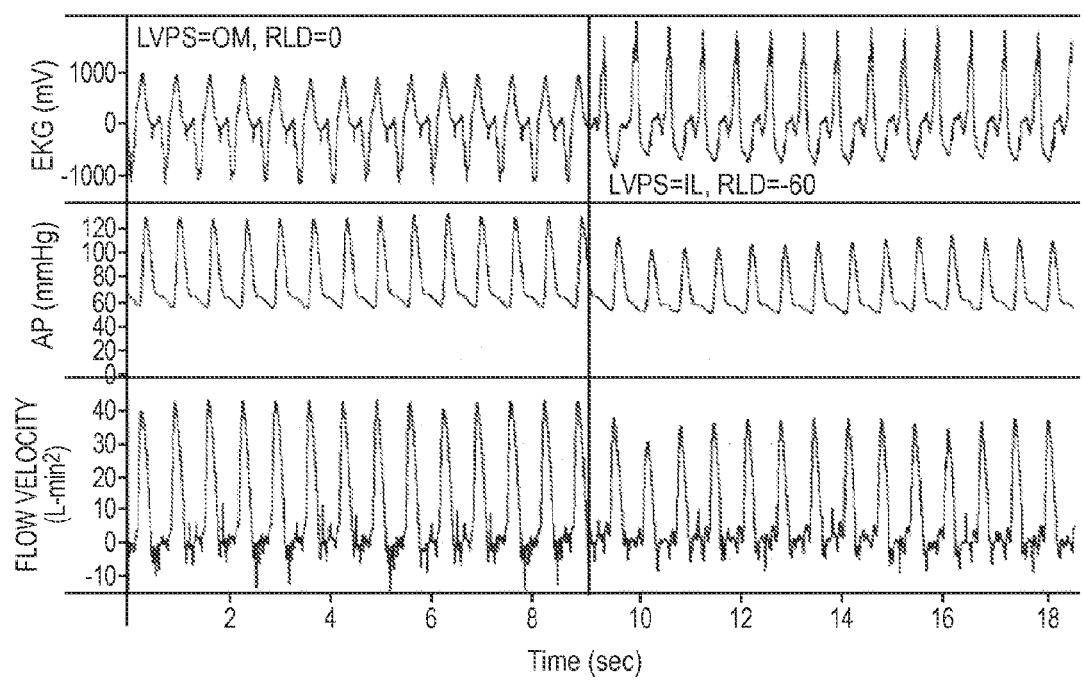
FIG. 8 depicts a representative change in EKG, arterial pressure (AP), and Aortic (Ao) flow velocity with a change in pacing settings.

Two weeks later, during permanent device implantation, testing was performed using PulseCO™. At a HR of 100 bpm, DDD BiVP was performed using 36 combinations of AVD and RLD in random order over 20 sec intervals. AVD was varied between 120 and 210 msec in 30 msec increments and RLD between +80 and −80 msec in 20 msec increments. Results were displayed as a response surface for AVD and RLD (FIG. 7). Pacing with an AVD of 120 msec and an RLD of −20 msec produced the best CO, with up to 19% improvement with optimal settings. Then, pacing with the optimal RLD (sequential BiVP) was compared to simultaneous BiVP (RLD=0 msec) and atrial pacing for 60 sec intervals (FIG. 8).

Sequential BiVP provided 8% improvement over simultaneous pacing and 29% improvement over atrial pacing alone.

These results show that: epicardial site-timing measurements are feasible clinically; optimization of both site and timing enhance cardiac output beyond effects achieved by optimizing either alone; "Monte Carlo" techniques are feasible and powerful in patients; surface plot analysis is clinically relevant; real-time BiVP optimization is feasible and clinically important; epicardial access to inferior and lateral surfaces of the left ventricle can provide new and important scientific information; epicardial optimization and lead insertion might convert endocardial nonresponders to responders or increase clinical benefit in a subset of "responders;" steady state improvement in cardiac output greater than 20% is achievable in selected patients.

Example 5

Design of Experiments (DOE) Methodology for Biventricular Pacing Optimization

Biventricular pacing (BiVP) is an important therapy for congestive heart failure, reversing intraventricular conduction delay and left ventricular (LV) dysfunction intrinsic to dilated cardiomyopathy. BiVP has not been carefully evaluated in acute heart failure, yet preliminary data suggest that BiVP may also be a valuable adjunct to the treatment of LV or right ventricular (RV) dysfunction after cardiac surgery for acquired or congenital heart disease, reducing the perioperative requirements for beta agonists, phosphodiesterase inhibitors, afterload reducing agents, diuretics, balloon pumps or LV assist devices. Acutely, BiVP is associated with improvements in systolic and diastolic function, cardiac index, energy consumption, interventricular synchrony and LV intraventricular synchrony. Studies investigating the possible added benefit of altering atrioventricular delay (AVD), RV-LV delay (RLD) and LV pacing site (LVPS) during BiVP have shown that these parameters can result in further significant acute increases in cardiac function with patient-specific optimization. These studies demonstrate that these parameters are important determinants of the efficacy of BiVP, but the relative importance and interaction between them have not been demonstrated. However, exploring all possible combinations of AVD, RLD, and LVPS requires more measurements than can be practically performed in the time available at the end of most cardiac surgeries.

Design of Experiments (DOE) methodology offers an organized approach that connects experiments in a rational manner, giving more precise information from fewer experiments. Factorial experimental design investigates all possible combinations of the levels of the factors. It is more efficient than one-factor-at-a-time experimentation and is necessary when interactions may be present to avoid misleading conclusions. As well, it allows the effects of a factor to be estimated at several levels of the other factors, yielding conclusions that are valid over a range of experimental conditions. One useful output of DOE is a response surface of the experimental region, which can be used to help optimize the response. By defining a suitable approximation of the true functional relationship between the response and the set of independent variables, one can estimate the optimum combination of factors. For instance, consider CO as a polynomial function of two inputs, AVD and RLD. The two-dimensional surface in space, (AVD,RLD,CO), can then be described by the function:

$$CO = f(AVD, RLD)$$

In general, the number of input variables can be unlimited, and the resulting surface becomes a hypersurface. If nothing else is known about the surface, then high-resolution sampling of the entire variable space is necessary. However, if some prior information is known about the response of the output to these variables, then 'intelligent' sampling can be performed, reducing the number of required measurement.

From prior experience, the shapes of the 1-dimensional CO response curves (examples being the AVD-CO and RLD-CO relations) during acute RV pressure overload are generally quadratic and smooth, with a relatively broad peak, so the curves may be reasonably approximated by a quadratic polynomial. Thus, when varying two factors, the 2-dimensional surface may be approximated by a quadratic response surface model:

$$CO=c_0+c_1(AVD)+c_2(RLD)+c_3(AVD)(RLD)+c_4(AVD)^2+c_5(RLD)^2$$

By implementing this design, the number of necessary measurements to find the optimum combination can be greatly reduced. The approximate location of the peak in CO can be rapidly established with a relatively small number of measurements and then be refined with a few additional measurements, thus reducing the time needed to determine the optimum settings. If more than two factors are being varied for optimization a more complex model is necessary.

As a preliminary study, simultaneous optimization of AVD and RLD was performed during BiVP in a pig model of acute RV pressure overload and implemented DOE methodology using algorithms available in Matlab (The Mathworks, Natick, Mass.).

In an open chest anesthetized pig, complete heart block was induced by ethanol ablation of the AV node. During epicardial DDD BiVP, aortic flow velocity was measured by ultrasonic aortic flow probe. AVD was increased from 60 to 180 msec in 30 msec increments. At each AVD, RLD was varied from +80 to −80 msec in 20 msec increments (positive values=RV first). Pacing remained at each setting for 10 sec. Measurements were taken during acute RV pressure overload, induced by snaring the pulmonary artery until cardiac output (CO) was halved. CO for each combination of settings was calculated by integrating the aortic flow tracing from three end-expiratory beats at the end of the pacing interval. The resulting measured response of CO was displayed as a response surface with AVD on the ordinate, RLD on the abscissa and variations in CO represented by a red-to-blue color map by linearly interpolating between measured values, with contour lines representing 5% changes in CO. To test whether DOE methodology could have been used to locate the approximate location of the peak in CO with fewer measurements, CO response from 15 of the 45 AVD-RLD combinations (AVD=[60, 120, 180]; RLD=[+80, +40, 0-40, −80]) was modeled by a quadratic response surface model and plotted in the same manner.

Figure 5:
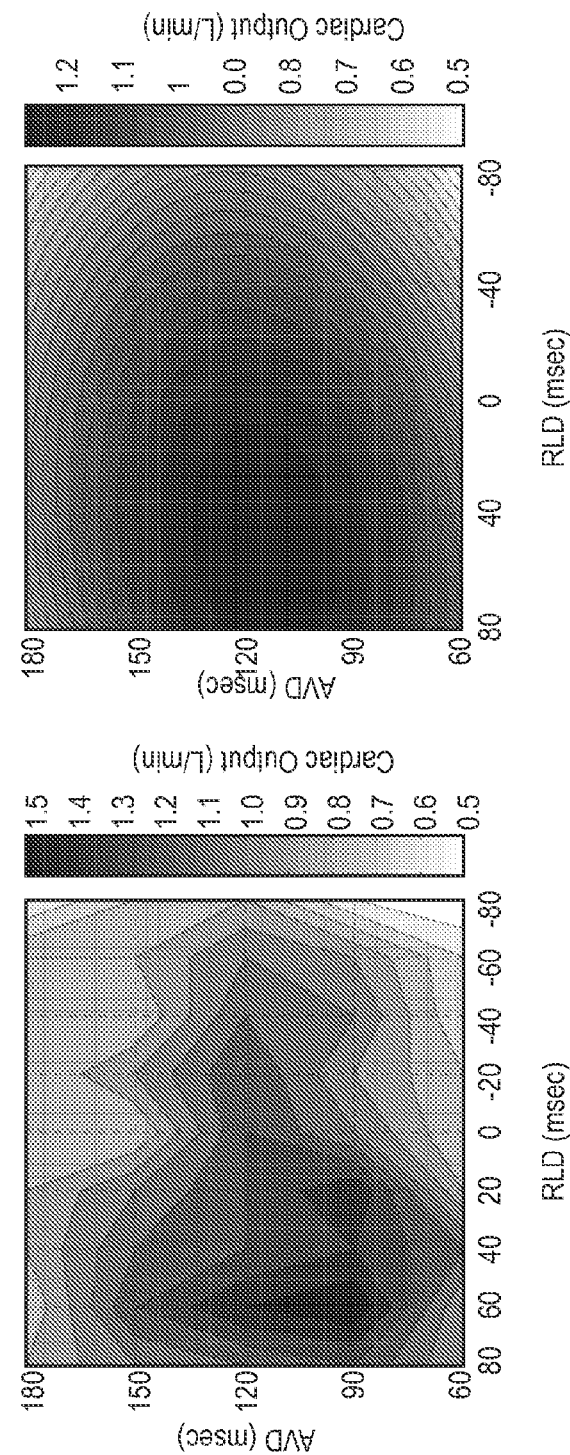
FIG. 5A-5B. illustrates cardiac output data for 45 combinations of AVD and RLD measured during critical PS/HB experiment (FIG. 5A).

Results of optimization of 45 AVD-RLD combinations during BiVP and the resulting quadratic response surface model from 15 of these points are shown in FIGS. 5A and 5B. CO was measured at 45 AVD-RLD combinations during acute RV pressure overload (FIG. 5A). CO from only 15 of these AVD-RLD combinations modeled by a quadratic response surface model (FIG. 5B).

When measurements were taken at 45 AVD-RLD combinations, the resulting optimum CO was 1.6 L/min at an AVD of 90 msec and an RLD of +60 msec, shown in the left panel of FIG. 1. When only 15 of these measured CO values were modeled by a quadratic response surface, the predicted optimum CO value was 1.3 L/min at an AVD of 115 msec and an RLD of +49 msec, shown in the right panel of FIG. 1. These two optimums occur in the same quadrant of the variable space. So, after estimation of the optimum settings, the best AVD-RLD combination could have been refined by taking further measurements in this quadrant, while still reducing the overall number of necessary measurements and thus the duration of data collection to find the optimum.

While the preliminary results suggest that using a quadratic response surface model may prove useful in reducing the number of necessary measurements to find optimum BiVP pacing settings and thus allow significant shortening of the duration of data collection, it may not work in all situations. In some cases there may be more complex interactions between the variables causing more than one peak in CO as different combinations of factors give local maxima. In another preliminary study, simultaneous optimization of LV pacing site (LVPS) and RLD were performed in the pig model. In this case, the CO response showed local maxima from two combinations of pacing settings, distinct in both LVPS and RLD, shown in FIG. 6. To overcome this problem, it may be possible to utilize more complex response surface models to estimate the local maxima. In conclusion, there is clear benefit to cardiac function from patient-specific BiVP optimization. To test the full range of potentially optimum pacing settings in patients using the present methods, however, will require 63 minutes of testing (7 AVD ' 9 RLD ' 6 LVPS ' 10 sec). In the clinical setting after cardiac surgery, the time available for testing is limited to approximately 10 min, and the shorter the duration of data collection the easier and more reliable the optimization. So there is the need for more than a 6-fold decrease in the time for data collection. On our first pass, by the use of DOE, we have demonstrated a method to reduce data collection by 2-3 fold. Further reduction will be necessary. To accomplish this, computer-driven automated setting changes as well as decreased pacing interval at each setting can be implemented.

Example 6

Left Ventricular Pacing Site-Timing Optimization During Biventricular Pacing Using a Multi-Electrode Patch A 71-year-old male with class IV congestive heart failure and an infected pacemaker/ICD underwent median sternotomy for removal of endocardial leads with a 15 mm vegetation. Biventricular pacing was optimized with an aortic flow probe, a multi-electrode left ventricular patch, and a randomized protocol assessing 54 combinations of pacing site and right ventricle-left ventricle delay. Results, assessed with response surface methodology, determined permanent epicardial lead position and timing. The difference between the best and worst site-timing combinations altered cardiac index by nearly 70%. This experience demonstrates potential importance of the epicardial approach to site-timing optimization for biventricular pacing.

A 71-year-old male with dilated cardiomyopathy and class IV congestive heart failure was referred for Staph epidermidis bacteremia. Transesophageal echocaraphy revealed a mobile, 15 mm echodensity on the right atrial lead of a dual chamber pacemaker/ICD system. QRS duration was 220 ins on ECG. Ejection fraction was estimated at 15%, with dysynchrony of the interventricular septum-left ventricular free wall and moderate mitral regurgitation.

The patient underwent median sternotomy with extraction of endocardial pacemaker/ICD leads on cardiopulmonary bypass (CPB) and removal of the ICD generator. In anticipation of permanent biventricular pacing (BiVP), temporary BiVP was tested before CPB. Mapping of the left ventricle (LV) was performed using an aortic flow probe, a multi-electrode patch, and a randomized protocol to identify the best lead position and right ventricle-left ventricle delay (RLD). 1-2 Permanent LV epicardial leads were implanted at the conclusion of the procedure and temporary leads were utilized for perioperative BIVP.

With informed consent, the chest was entered through a standard midline sternotomy, and a pericardial well was created. The pericardial space was free of adhesions with clear fluid. During anticoagulation, cannulation, and excision of the ICD generator and leads from the chest wall, temporary pacing was established via the right atrial appendage and anterior right ventricle (RV). An epicardial pacing array incorporating 6 bipolar pacing leads was placed behind the posterolateral LV and connected to a temporary pacing box containing a Medtronic InSync III pacemaker (Medtronic Inc, Minneapolis, Minn.). A 90 mm electromagnetic flow probe (Carolina Medical Inc, King, N.C.) was placed around the ascending aorta. DDD BiVP was initiated at a heart rate of 90 and atrioventricular delay of 150 ms. Fifty-four combinations of nine RLDs and six LV sites were tested at 15-second intervals in a randomized sequence. The LV sites were apex, infero-medial, infero-lateral, posterior descending, circumflex, and obtuse margin. The RLDs covered a range from 80 msec with RV first to 80 msec with LV first in 20 msec increments.

Data Acquisition and Analysis:

Analog data for electrocardiogram, arterial pressure, and aortic flow velocity were sampled and transferred through a 16 channel analog to digital converter (MacLab, ADInstruments Inc, Milford, Mass.) to a personal computer (iMac, Apple Computer, Cupertino, Calif.). Data were then imported into MATLAB (The MathWorks, Inc., Natick, Mass.). Using customized routines, a relatively small number of arrhythmic beats were eliminated. Aortic Flow was averaged over each 15-second interval to give CO and divided by body surface area to give cardiac index (CI). Results were plotted using response surface methodology producing a two-dimensional plot in which CI was indicated by color.

After removal of the infected leads and closure of the atriotomy, permanent epicardial pacing leads were positioned on the LV epicardium directly over the circumflex site on the pacing array. Temporary leads were placed in the right atrial appendage, anterior right ventricle, and circumflex and obtuse marginal sites of the LV. The patient was weaned from CPB with temporary BiVP and dobutamine and transferred to the intensive care unit. The permanent leads were capped and stored in a subcutaneous pocket in the right upper abdomen. As there was little advantage of an RLD offset, with simultaneous BiVP was implemented with and RLD=0 msec.

Pacing the obtuse marginal site at a RLD of −40 or 0 and the circumflex site at an RLD of 0 yielded the highest CI, 64-66% greater than the worst combination, pacing at the infero-lateral site at a RLD of −80. A response surface plot of CI from each LV site/RLD combination was obtained. This plot was constructed retrospectively, permitting greater insight into the effects of BiVP in this patient than was available during real time analysis in the operating room.

The patient was discharged from the hospital after completion of antibiotic therapy and implantation of a new pacemaker/ICD with biventricular pacing capability. BiVP was objectively compared to no pacing on several occasions. On the first postoperative day, CI increased 20% with BiVP. At the time of permanent pacemaker/ICD implantation, initiation of BiVP increased radial artery systolic pressure from 103 to 140 mm Hg in 15 seconds.

Clinical trials have demonstrated that addition of an LV pacing lead via the coronary sinus to standard RA/RV DDD lead configurations can narrow the QRS, improve exercise capacity and quality of life, and reduce mortality in patients with severe heart failure and intraventricular conduction delays. The patient described in this report meets current criteria for implementation of BiVP.

Studies of endocardial BiVP differ in suggesting that cardiac function is maximized by localization of LV pacing leads in the mid-lateral region of the LV 3-4 or other locations. Endocardial LV lead position is limited by anatomy of the cardiac veins. Furthermore, many locations are unstable or inaccessible, resulting in implantation failure in 5-14% of attempts. Consequently, only a limited subset of LV pacing sites have been mapped, and the relative importance of site and timing in BiVP have been inferred but not directly measured. Advantages of the surgical approach to the entire LV epicardium are illustrated by the present report. Thoracoscopy has been used to map the epicardial surface of the LV, but randomized study of site and timing has not previously been reported. The surgical procedure described in this report allowed BiVP optimization under an IRB approved protocol. The effect of posterior, inferior, and lateral LV pacing as well as timing were defined, and a distinct effect of both LV site and RLD on CI was demonstrated. This case report is based on acute hemodynamic during thoracotomy in an anesthetized patient. The relation between these effects correlate with a long-term benefit remains to be proven. Clinical studies are warranted to address this issue.

The hemodynamic benefits of BiVP in this patient were particularly profound. BiVP is more likely to be effective as ejection fraction decreases and intraventricular conduction delay, LV dyssynchrony, and mitral regurgitation increase. Our patient's cardiomyopathy was relatively advanced in all of these respects. The precise mechanism of benefit in this patient can include restoration of synchronous contraction of the free wall and septum, reduction of mitral regurgitation, or both. Results indicate that BiVP optimization can increase CO by 66% when best and worst pacing protocols are compared and provide a rational basis for additional studies aimed at maximizing the clinical response to pacing for heart failure.

APPENDIX

TABLE 1

Pacing Protocol -- Table showing the pacing protocol used and elapsed time in seconds.

| AVD test | AVD | Time (sec) | VPS test | VPS | Time (sec) | OPT/BL test | Time (sec) |
|---|---|---|---|---|---|---|---|
| VPS = RV | 90 | 10 | AVD = OPT | RV | 140 | OPT | 220 |
| | 120 | 20 | | BiV | 150 | BL | 250 |
| | 150 | 30 | | LV | 160 | | |
| | 180 | 40 | | RV | 170 | | |
| | 210 | 50 | | BiV | 180 | | |
| | 240 | 60 | | LV | 190 | | |
| | 270 | 70 | | | | | |
| | 240 | 80 | | | | | |
| | 210 | 90 | | | | | |
| | 180 | 100 | | | | | |
| | 150 | 110 | | | | | |
| | 120 | 120 | | | | | |
| | 90 | 130 | | | | | |

AVD = Atrioventricular Delay, BL = Baseline, LV = Left Ventricle, OPT = Optimum, RV = Right Ventricle, VPS = Ventricular Pacing Site.

What is claimed is:

1. A method for selection of optimal parameters for permanent pacing, the method comprising:
   (a) positioning one or more arrays of lead wires in the posterior pericardium of a subject, wherein the arrays are connected to a multiplexing switch, wherein the switch is connected to a computer processor and a biventricular pacemaker;
   (b) from the computer processor, generating a randomized sequence of: (i) pacing sites (VPS), (ii) right ventricular-left ventricular delays (RLDs), (iii) heart rates (HR); (iv) atrioventricular delays (AVDs), (v) or any combination or permutation thereof; and
   (c) determining cardiac output in real time, using aortic flow velocity, thereby allowing selection of optimal parameters for permanent pacing.

2. The method of claim 1, wherein the processor automatically implements the randomized sequence of VPS/RLD/HRJAVD combinations while recording aortic flow_via the aortic flow probe.

3. The method of claim 1, wherein the computer processor selects a parameter combination producing the highest cardiac output.

4. The method of claim 1, further comprising displaying results regarding parameter combinations for permanent pacing.

5. The method of claim 1, wherein a heart rate permutation is from about 60 to about 100 beats per minute.

6. The method of claim 1, wherein an AVD permutation is from about 90 to about 300 msec.

7. The system of claim 1, wherein a RLD permutation is from about −80 to about +80 msec.

* * * * *